US012558053B2

(12) United States Patent
Kopel et al.

(10) Patent No.: US 12,558,053 B2
(45) Date of Patent: Feb. 24, 2026

(54) SYSTEMS AND METHODS OF ASSESSING BREATH HOLD DURING INTRAPROCEDURAL IMAGING

(71) Applicant: Covidien LP, Mansfield, MA (US)

(72) Inventors: Evgeni Kopel, Barkan (IL); Michael E. Calcutt, Burnsville, MN (US); Oren P. Weingarten, Hod-Hasharon (IL); Ariel Birenbaum, Raanana (IL); Ofer Barasofsky, Tel Mond (IL)

(73) Assignee: Covidien LP, Mansfield, MA (US)

( * ) Notice: Subject to any disclaimer, the term of this patent is extended or adjusted under 35 U.S.C. 154(b) by 55 days.

(21) Appl. No.: 18/288,953

(22) PCT Filed: May 23, 2022

(86) PCT No.: PCT/IB2022/054810
§ 371 (c)(1),
(2) Date: Oct. 30, 2023

(87) PCT Pub. No.: WO2022/249035
PCT Pub. Date: Dec. 1, 2022

(65) Prior Publication Data
US 2024/0225584 A1     Jul. 11, 2024

Related U.S. Application Data

(60) Provisional application No. 63/194,695, filed on May 28, 2021.

(51) Int. Cl.
| | |
|---|---|
| *A61B 6/00* | (2024.01) |
| *A61B 6/46* | (2024.01) |
| *A61B 34/20* | (2016.01) |

(52) U.S. Cl.
CPC .............. *A61B 6/527* (2013.01); *A61B 6/466* (2013.01); *A61B 6/487* (2013.01); *A61B 6/5235* (2013.01);
(Continued)

(58) Field of Classification Search
CPC ......... A61B 6/527; A61B 6/466; A61B 6/487; A61B 6/5235; A61B 6/54; A61B 6/032;
(Continued)

(56) References Cited

U.S. PATENT DOCUMENTS

| | | | |
|---|---|---|---|
| 2002/0035321 A1 | 3/2002 | Bucholz et al. | |
| 2004/0254773 A1* | 12/2004 | Zhang | .................... A61B 6/541 703/11 |

(Continued)

FOREIGN PATENT DOCUMENTS

| | | |
|---|---|---|
| WO | 2021092116 A1 | 5/2021 |

OTHER PUBLICATIONS

PCT Search Report and Written Opinion issued in PCT Application No. PCT/IB2022/054810 dated Sep. 1, 2022.

*Primary Examiner* — Sean D Mattson
(74) *Attorney, Agent, or Firm* — Weber Rosselli & Cannon LLP

(57) ABSTRACT

A system and method for improving a quality of images for local registration where a position of a sensor is monitored to determine whether a breath hold plateau has been achieved, and following imaging is monitored to determine whether the sensor position has returned to a pre-breath hold position.

20 Claims, 16 Drawing Sheets

(52) U.S. Cl.
CPC ................ *A61B 6/54* (2013.01); *A61B 34/20*
(2016.02); *A61B 2034/2051* (2016.02); *A61B*
*2034/2061* (2016.02)

(58) Field of Classification Search
CPC ....... A61B 6/4085; A61B 6/4441; A61B 6/12;
A61B 34/20; A61B 2034/2051; A61B
2034/2061
See application file for complete search history.

(56) References Cited

U.S. PATENT DOCUMENTS

| 2005/0113673 | A1* | 5/2005 | Avinash | ................ | A61B 6/541 |
| | | | | | 600/509 |
| 2008/0118135 | A1* | 5/2008 | Averbuch | ................ | G06T 7/11 |
| | | | | | 382/131 |
| 2017/0156685 | A1 | 6/2017 | Dickhans et al. | | |
| 2020/0046433 | A1* | 2/2020 | Krimsky | ............... | A61B 34/20 |
| 2021/0030482 | A1 | 2/2021 | Alexandroni et al. | | |

* cited by examiner

400

SYSTEMS AND METHODS OF ASSESSING BREATH HOLD DURING INTRAPROCEDURAL IMAGING

TECHNICAL FIELD

This disclosure relates to the field of navigation of and maintaining position of medical devices, such as biopsy or ablation tools, relative to targets.

DESCRIPTION OF RELATED ART

There are several commonly applied medical methods, such as endoscopic procedures or minimally invasive procedures, for treating various maladies affecting organs including the liver, brain, heart, lungs, gall bladder, kidneys, and bones. Often, one or more imaging modalities, such as magnetic resonance imaging (MRI), ultrasound imaging, computed tomography (CT), or fluoroscopy are employed by clinicians to identify and navigate to areas of interest within a patient and ultimately a target for biopsy or treatment. In some procedures, pre-operative scans may be utilized for target identification and intraoperative guidance. However, real-time imaging may be required to obtain a more accurate and current image of the target area. Furthermore, real-time image data displaying the current location of a medical device with respect to the target and its surroundings may be needed to navigate the medical device to the target in a safe and accurate manner (e.g., without causing damage to other organs or tissue).

For example, an endoscopic approach has proven useful in navigating to areas of interest within a patient, and particularly so for areas within luminal networks of the body such as the lungs. To enable the endoscopic approach, and more particularly the bronchoscopic approach in the lungs, endobronchial navigation systems have been developed that use previously acquired MRI data or CT image data to generate a three-dimensional (3D) rendering, model, or volume of the particular body part such as the lungs.

The resulting volume generated from the MRI scan or CT scan may be utilized to create a navigation plan to facilitate the advancement of a navigation catheter (or other suitable medical device) through a bronchoscope and a branch of the bronchus of a patient to an area of interest. A locating or tracking system, such as an electromagnetic (EM) tracking system, may be utilized in conjunction with, for example, CT data, to facilitate guidance of the navigation catheter through the branch of the bronchus to the area of interest. In certain instances, the navigation catheter may be positioned within one of the airways of the branched luminal networks adjacent to, or within, the area of interest to provide access for one or more medical instruments.

However, local registration may be required to eliminate so called CT-to-body divergence. Improvements to these local registration techniques are always desired.

SUMMARY

One aspect of the disclosure is directed to a system including: a catheter including a sensor on a distal portion thereof; a computing device including a processor and a computer readable recording medium, the computing device configured to receive signals from the sensor to determine a position of the distal portion of the catheter. The computing device is further configured to receive a fluoroscopic video of the catheter proximate a target. The computing device is further configured to monitor a position of the sensor to determine whether a breath hold plateau has been achieved. The computing device is further configured to determine whether movement of the sensor has exceeded a threshold to achieve the breath hold plateau. The computing device is further configured to cease fluoroscopic image video acquisition. The computing device is further configured to monitor the position of the sensor, to determine whether the sensor position has returned to a pre-breath hold position, where upon determination that the sensor has returned to a pre-breath hold position. The computing device is further configured to determine a relative position of the catheter and the target at multiple instances in the fluoroscopic video. The computing device is further configured to calculate a position of the target in a coordinate system of the sensor. The computing device is further configured to update a displayed position of the distal end of the catheter with respect to the target in a 3D model. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The system where the 3D model is derived from a pre-procedure CT image data. The system where in the sensor on the distal portion of the catheter is an electromagnetic sensor. The system where position of the target is calculated based on the calculated offset and a detected position of the sensor. The system where a breath hold is begun after reception of fluoroscopic images is initialized. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

A further aspect of the disclosure is directed to a method of improving a quality of images for local registration, including: initializing imaging. The method also includes monitoring a position of a sensor to determine whether a breath hold plateau has been achieved. The method also includes determining whether movement of the sensor has exceeded a threshold to achieve the breath hold plateau. The method also includes ceasing imaging. The method also includes monitoring the position of the sensor, to determine whether the sensor position has returned to a pre-breath hold position, where upon determination that the sensor has returned to a pre-breath hold position finalizing local registration. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method further including initiating a breath hold of a patient after initializing imaging. The method further including ceasing breath hold prior to determining whether the sensor has returned to a pre-breath hold position. The method where if the movement of the sensor to reach the breath hold plateau exceeds a threshold the method further includes: ending a breath hold. The method may also include returning to normal tidal volume breathing. The method may also include reinitializing imaging. The method where if the position of the sensor does not return to the pre-breath hold position local registration is restarted. The method where finalizing local registration includes: determining a position of a distal end of a catheter in which the sensor is located. The method may also include determining a position of a target. The method may also include calculating an offset between the distal end of the catheter and the target. The method may also include updating a displayed position of the distal end of the catheter with respect to the target in a 3D model. The method where the 3D model is derived from a pre-procedure CT image data. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Another aspect of the disclosure is directed to a method of navigating a catheter to a desired location within a luminal network including: receiving a CT image data set, identifying one or more targets in the CT image data set, generating a three-dimensional (3D) model of the luminal network and pathway to the one or more targets, registering the 3D model and pathway to a luminal network, updating the position of the catheter in the 3D model as the along the pathway proximate one of the targets, performing a local registration to determine a relative position of the catheter and one of the targets, acquiring a fluoroscopic image of the luminal network. The method also includes monitoring a position of a sensor associated with the catheter to determine whether a breath hold plateau has been achieved. The method also includes determining whether movement of the sensor has exceeded a threshold to achieve the breath hold plateau. The method also includes ceasing fluoroscopic image acquisition. The method also includes monitoring the position of the sensor, to determine whether the sensor position has returned to a pre-breath hold position, where upon determination that the sensor has returned to a pre-breath hold position; determining a position of the target and the catheter in the fluoroscopic image, detecting a position of a sensor on a distal portion of the catheter, calculating a position of the target in a coordinate system of the sensor, and updating a displayed position of the distal end of the catheter with respect to the target in the 3D model. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method where the sensor is an electromagnetic sensor. The method where the sensor is a fiber-Bragg grating shape sensor. The method where position of the target is calculated based on the calculated offset and the detected position of the sensor. The method further including initiating a breath hold of a patient after initializing of acquisition of fluoroscopic images. The method further including ending breath hold prior to determining whether the sensor has returned to a pre-breath hold position. The method where if movement of the sensor to reach the breath hold plateau exceeds a threshold the method further includes: ending a breath hold. The method may also include returning to normal tidal volume breathing. The method may also include reinitializing imaging. The method where if the position of the sensor does not return to the pre-breath hold position local registration is restarted. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

BRIEF DESCRIPTION OF THE DRAWINGS

Various aspects and embodiments of the disclosure are described hereinbelow with references to the drawings, wherein.

DETAILED DESCRIPTION

Figure 1:
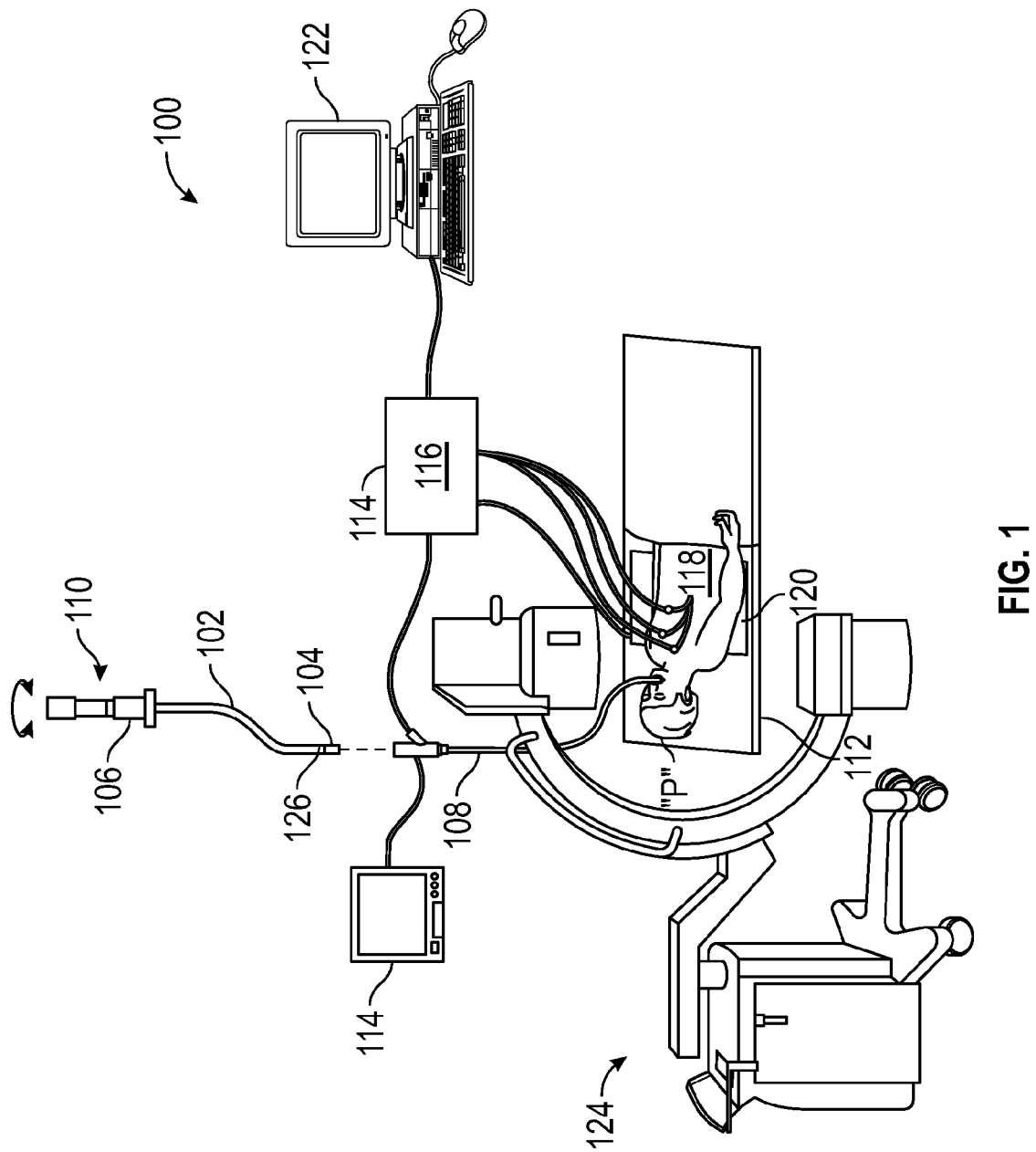
FIG. 1 is a schematic diagram of a system for navigating to soft-tissue targets via luminal networks in accordance with the disclosure.

The acquisition of intraprocedural images is a common method of making assessments of navigation of a catheter or tool to a location within the patient. In instances where a 3D volume is generated from the acquired intraprocedural images, minimization of the movement of the tissues being imaged is desirable. Limiting movement of the tissues ensures that higher quality images (e.g., without blur or artifacts) can be acquired and the higher quality images ensure that any 3D volume to be generated from the images is also of higher quality allowing for more accurate analysis. To assist in this, a patient is often sedated to bring their heart rate to a relative constant. Further during a procedure, the patient, who is typically intubated and ventilated may have their breathing controlled at a normal tidal volume breathing. In this way there are no large inhalations or expirations to provide a stable physiology for the clinician during the procedure. Still further, particularly when acquiring images of the patient's chest and lungs, a breath hold can be requested by the clinician and executed by the anesthesiologist. Once achieved, the lungs are held at a substantially constant level of inflation with minimal movement allowing for highly accurate imaging and 3D volume generation.

However, sometimes during a procedure the clinician may forget to make the request for a breath hold. Other times, because the clinician is not the one performing the breath hold, he or she has no understanding of how well the breath hold was performed, or if as a result of the breath hold the physiology of the patient changed dramatically, even after they have returned to normal tidal volume breathing. The result is that when seeking to acquire a biopsy, the location of a catheter or biopsy tools may be dramatically different in the patient than either a detected position or a position determined by the intraprocedural imaging. The result is that a biopsy sample may be taken of the wrong tissue and tissue biopsied may not in fact be the previously identified tumor or lesion. In a similar fashion where treatment is undertaken, where the placement of a therapeutic tool (e.g., and RF or microwave ablation catheter) within a tumor or lesion is critical, a faulty or incorrectly performed breath hold may result in improper placement of the therapeutic tool.

One aspect of the disclosure is directed to ensuring that a breath hold is acquired during the workflow of an intraluminal navigation in, for example, the lungs. Further aspects of the disclosure are directed to methods of alerting a clinician to the insufficiency of the breath hold during the intraprocedural imaging. Still further aspects are to alerting the clinician to changes in breathing patterns during or following a breath hold procedure. Additional aspects of the disclosure are directed to providing a record that can be stored with the patient of the breath hold for further analysis after the procedure for both confirmation of the effectiveness of the breath hold and for additional assessments.

In accordance with the disclosure, a 3D volume of a patient's lungs or another suitable portion of the anatomy, may be generated from previously acquired scans, such as CT scans. These scans may be used to generate a 3D model of the anatomy. The 3D model and related scan data are used to identify targets, e.g., potential lesions for biopsy or treatment, and to generate a pathway plan through the anatomy to reach the targets.

Once the pathway plan is generated and accepted by a clinician, that pathway plan may be utilized by a navigation system to drive a catheter along the pathway plan through the anatomy to reach the desired target. The driving of the catheter along the pathway plan may be manual or it may be robotic, or a combination of both. Manual systems include the ILLUMISITE navigation system sold by Medtronic PLC, robotic systems include the ION system sold by Intuitive Surgical Inc. and the MONARCH system sold by Auris Health, Inc. In a single procedure planning, registration of the pathway plan to the patient, and navigation are performed to enable a medical device, e.g., a catheter to be navigated along the planned path to reach a target, e.g., a lesion, so that a biopsy or treatment of the target can be completed.

As noted above, whether manual or robotic, the pathway plan and 3D model developed from the pre-procedure scan data must be registered to the patient before navigation of the catheter to a target within the anatomy can begin. Once registered, a catheter or other tool may be navigated following the pathway plan to a desired location. While this registration is generally more that suitable for general navigation of the pathway, regardless of the registration method employed, and there are numerous registration methods, the 3D model and pathway plan may still not provide sufficient accuracy for the "last mile" of navigation allowing for the guidance of medical devices or instruments into the target for biopsy and treatment.

In some cases, the inaccuracy is caused by deformation of the patient's lungs during the procedure relative to the lungs at the time of the acquisition of the previously acquired CT data. This deformation (CT-to-Body divergence) may be caused by many different factors including, for example, changes in the body when transitioning from between a non-sedated state during the imaging to a sedated state during the procedure, the bronchoscope changing the patient's pose, the bronchoscope and catheter pushing the tissue, different lung volumes (e.g., the CT scans are acquired during full breath hold following inhale while navigation is typically performed while the patient is breathing at normal tidal breathing), different beds, different days, etc. Thus, an intraprocedural imaging modality may be employed to assist in visualizing medical devices and targets in real-time and enhance the accuracy of the navigation procedure.

In navigating the medical device to the target, clinicians may use a fluoroscopic imaging to visualize the position of the medical device relative to the target. While fluoroscopic images show highly dense objects, such as metal tools, bones, and large soft-tissue objects, e.g., the heart, the fluoroscopic images may not clearly show small soft-tissue objects of interest, such as lesions. Furthermore, the fluoroscopic images are two-dimensional (2D) projections which makes determining depths in the view difficult.

X-ray volumetric reconstruction has been developed to enable identification of soft tissue objects and to update the relative position of the target and the catheter in the pathway plan and 3D model. The volumetric reconstruction is made from a series of 2D fluoroscopic images taken at different angles to the tissue in question. In one method described in greater detail below, updating of the pathway plan and relative positions of the catheter and target can be achieved with a local registration process. This local registration process reduces CT-to-body divergence. After the local registration process, in one embodiment a locatable guide (i.e., a catheter with multiple sensors) may be removed from the catheter and a medical device, e.g., a biopsy tool, is introduced into the catheter for navigation to the target to perform the biopsy or treatment of the target, e.g., the lesion. However, as noted above the quality of the X-ray volumetric reconstruction is a function of the quality of the intraprocedural images, accordingly, the disclosure is directed to methods of the quality of these images by assessing the breath hold.

In accordance with aspects of the disclosure, and as noted above, the visualization of intra-body navigation of a medical device, e.g., a biopsy tool, towards a target, e.g., a lesion, may be a portion of a larger workflow of a navigation system, such as an electromagnetic navigation system. FIG. 1 is a perspective view of an exemplary system for facilitating navigation of a medical device, e.g., a catheter to a soft-tissue target via airways of the lungs. System 100 may be further configured to construct fluoroscopic based three-dimensional volumetric data of the target area from 2D fluoroscopic images to confirm navigation to a desired location. System 100 may be further configured to facilitate approach of a medical device to the target area by using Electromagnetic Navigation (EMN) and for determining the location of a medical device with respect to the target. One such EMN system is the ILLUMISITE system currently sold by Medtronic PLC, though other systems for intraluminal navigation are considered within the scope of the disclosure, as noted above.

One aspect of the system 100 is a software component for reviewing of computed tomography (CT) image scan data that has been acquired separately from system 100. The review of the CT image data allows a user to identify one or more targets, plan a pathway to an identified target (planning phase), navigate a catheter 102 to the target (navigation phase) using a user interface on computing device 122, and confirming placement of a sensor 104 relative to the target. The target may be tissue of interest identified by review of the CT image data during the planning phase. Following navigation, a medical device, such as a biopsy tool or other tool, may be inserted into catheter 102 to obtain a tissue sample from the tissue located at, or proximate to, the target.

As shown in FIG. 1, catheter 102 is part of a catheter guide assembly 106. In practice, catheter 102 is inserted into a bronchoscope 108 for access to a luminal network of the patient P. Specifically, catheter 102 of catheter guide assembly 106 may be inserted into a working channel of bronchoscope 108 for navigation through a patient's luminal network. A locatable guide (LG) 110 (a second catheter), including a sensor 104 is inserted into catheter 102 and locked into position such that sensor 104 extends a desired distance beyond the distal tip of catheter 102. The position and orientation of sensor 104 relative to a reference coordinate system, and thus the distal portion of catheter 102, within an electromagnetic field can be derived. Catheter guide assemblies 106 are currently marketed and sold by Medtronic PLC under the brand names SUPERDIMEN-SION® Procedure Kits, or EDGE™ Procedure Kits, and are contemplated as useable with the disclosure.

System 100 generally includes an operating table 112 configured to support a patient P, a bronchoscope 108 configured for insertion through patient P's mouth into patient P's airways; monitoring equipment 114 coupled to bronchoscope 108 (e.g., a video display, for displaying the video images received from the video imaging system of bronchoscope 108); a locating or tracking system 114 including a locating module 116, a plurality of reference sensors 118 and a transmitter mat 120 including a plurality of incorporated markers; and a computing device 122 including software and/or hardware used to facilitate identification of a target, pathway planning to the target, navigation of a medical device to the target, and/or confirmation and/or determination of placement of catheter 102, or a suitable device therethrough, relative to the target. Computing device 122 may be similar to workstation 1401 of FIG. 14 and may be configured to execute the methods of the disclosure including the method of FIG. 13.

A fluoroscopic imaging device 124 capable of acquiring fluoroscopic or x-ray images or video of the patient P is also included in this particular aspect of system 100. The images, sequence of images, or video captured by fluoroscopic imaging device 124 may be stored within fluoroscopic imaging device 124 or transmitted to computing device 122 for storage, processing, and display. Additionally, fluoroscopic imaging device 124 may move relative to the patient P so that images may be acquired from different angles or perspectives relative to patient P to create a sequence of fluoroscopic images, such as a fluoroscopic video. The pose of fluoroscopic imaging device 124 relative to patient P and while capturing the images may be estimated via markers incorporated with the transmitter mat 120. The markers are positioned under patient P, between patient P and operating table 112 and between patient P and a radiation source or a sensing unit of fluoroscopic imaging device 124. The markers incorporated with the transmitter mat 120 may be two separate elements which may be coupled in a fixed manner or alternatively may be manufactured as a single unit. Fluoroscopic imaging device 124 may include a single imaging device or more than one imaging device. As an alternative a cone-beam CT imaging device may be employed without departing from the scope of the disclosure and can be used to confirm the location of a tool within the patient, update CT-based 3D modeling, or replaced pre-procedural 3D modeling with intra-procedural modeling of the patient's airways and the position of the catheter 102 within the patient.

Computing device 122 may be any suitable computing device including a processor and storage medium, wherein the processor is capable of executing instructions stored on the storage medium. Computing device 122 may further include a database configured to store patient data, CT data sets including CT images, fluoroscopic data sets including fluoroscopic images and video, fluoroscopic 3D reconstruction, navigation plans, and any other such data. Although not explicitly illustrated, computing device 122 may include inputs, or may otherwise be configured to receive, CT data sets, fluoroscopic images/video and other data described herein. Additionally, computing device 122 includes a display configured to display graphical user interfaces. Computing device 122 may be connected to one or more networks through which one or more databases may be accessed.

With respect to the planning phase, computing device 122 utilizes previously acquired CT image data for generating and viewing a three-dimensional model or rendering of patient P's airways, enables the identification of a target on the three-dimensional model (automatically, semi-automatically, or manually), and allows for determining a pathway through patient P's airways to tissue located at and around the target. More specifically, CT images acquired from previous CT scans are processed and assembled into a three-dimensional CT volume, which is then utilized to generate a three-dimensional model of patient P's airways. The three-dimensional model may be displayed on a display associated with computing device 122, or in any other suitable fashion. Using computing device 122, various views of the three-dimensional model or enhanced two-dimensional images generated from the three-dimensional model are presented. The enhanced two-dimensional images may possess some three-dimensional capabilities because they are generated from three-dimensional data. The three-dimensional model may be manipulated to facilitate identification of target on the three-dimensional model or two-dimensional images, and selection of a suitable pathway through patient P's airways to access tissue located at the target can be made. Once selected, the pathway plan, three-dimensional model, and images derived therefrom, can be saved and exported to a navigation system for use during the navigation phase(s). The ILLUMISITE software suite currently sold by Medtronic PLC includes one such planning software.

With respect to the navigation phase, a six degrees-of-freedom electromagnetic locating or tracking system 114, or other suitable system for determining position and orientation of a distal portion of the catheter 102, is utilized for performing registration of the images and the pathway for navigation. Tracking system 114 includes the tracking module 116, a plurality of reference sensors 118, and the transmitter mat 120 (including the markers). Tracking system 114 is configured for use with a locatable guide 110 and particularly sensor 104. As described above, locatable guide 110 and sensor 104 are configured for insertion through catheter 102 into patient P's airways (either with or without bronchoscope 108) and are selectively lockable relative to one another via a locking mechanism.

Transmitter mat 120 is positioned beneath patient P. Transmitter mat 120 generates an electromagnetic field around at least a portion of the patient P within which the position of a plurality of reference sensors 118 and the sensor 104 can be determined with use of a tracking module 116. A second electromagnetic sensor 126 may also be incorporated into the end of the catheter 102. The second electromagnetic sensor 126 may be a five degree-of-freedom sensor or a six degree-of-freedom sensor. One or more of reference sensors 118 are attached to the chest of the patient P. Registration is generally performed to coordinate locations of the three-dimensional model and two-dimensional images from the planning phase, with the patient P's airways as observed through the bronchoscope 108, and allow for the navigation phase to be undertaken with knowledge of the location of the sensor 104.

Registration of the patient P's location on the transmitter mat 120 may be performed by moving sensor 104 through the airways of the patient P. More specifically, data pertaining to locations of sensor 104, while locatable guide 110 is moving through the airways, is recorded using transmitter mat 120, reference sensors 118, and tracking system 114. A shape resulting from this location data is compared to an interior geometry of passages of the three-dimensional model generated in the planning phase, and a location correlation between the shape and the three-dimensional model based on the comparison is determined, e.g., utilizing the software on computing device 122. In addition, the software identifies non-tissue space (e.g., air filled cavities) in the three-dimensional model. The software aligns, or registers, an image representing a location of sensor 104 with the three-dimensional model and/or two-dimensional images generated from the three-dimension model, which are based on the recorded location data and an assumption that locatable guide 110 remains located in non-tissue space in patient P's airways. Alternatively, a manual registration technique may be employed by navigating the bronchoscope 108 with the sensor 104 to pre-specified locations in the lungs of the patient P, and manually correlating the images from the bronchoscope to the model data of the three-dimensional model.

Though described herein with respect to EMN systems using EM sensors, the instant disclosure is not so limited and may be used in conjunction with flexible sensor, shape sensors such as Fiber-Bragg gratings, ultrasonic sensors, or without sensors. Additionally, the methods described herein may be used in conjunction with robotic systems such that robotic actuators drive the catheter 102 or bronchoscope 108 proximate the target.

Figure 2:
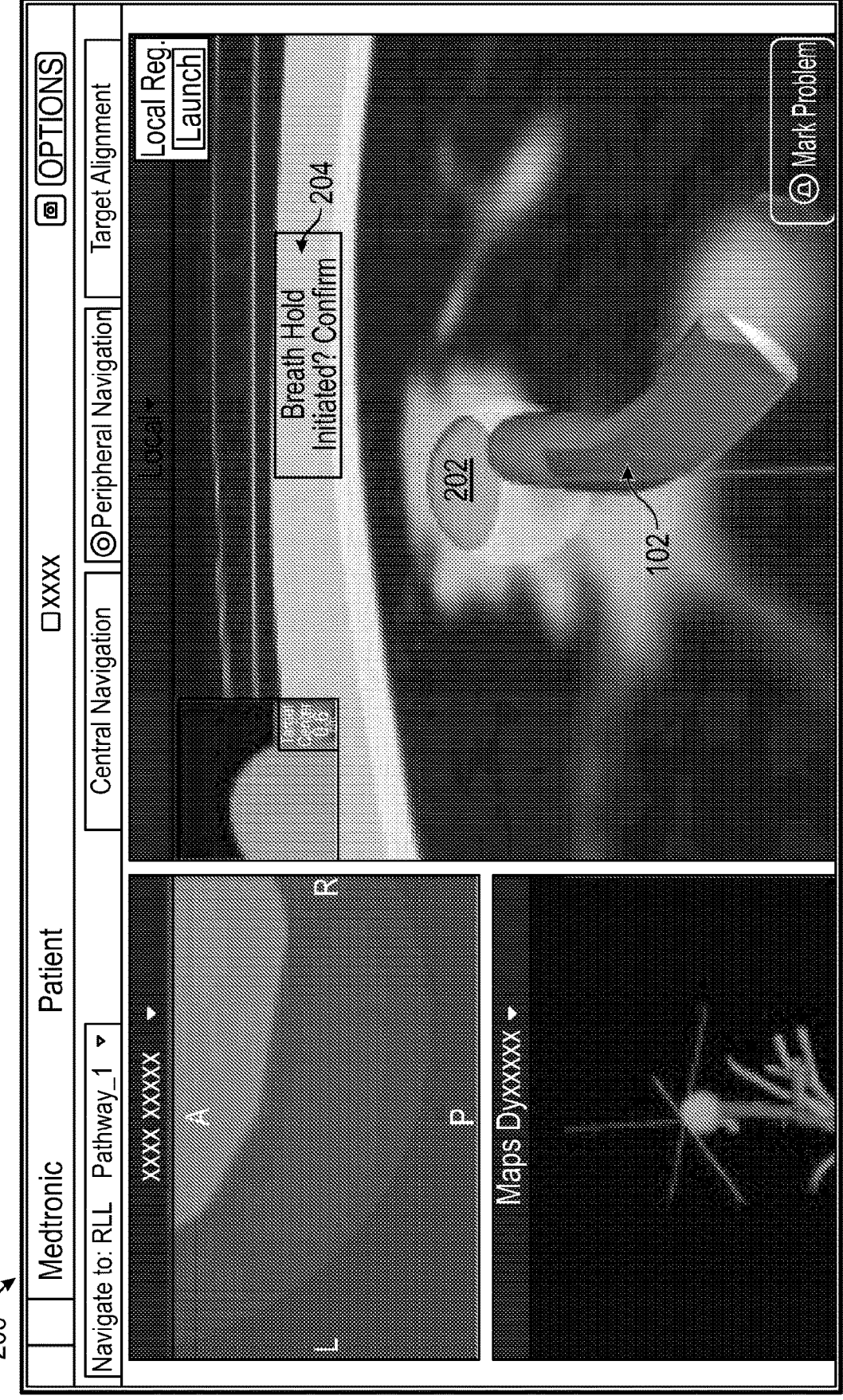
FIG. 2 is a user interface of a navigation program in accordance with aspects of the disclosure.

Following registration of the patient P to the image data and pathway plan, a user interface 200 as shown in FIG. 2 is displayed on the computing device 122 using the navigation software which sets forth the pathway that the clinician is to follow to reach the target. Once catheter 102 has been successfully navigated proximate, as shown in FIG. 2, the target 202 a local registration process may be performed for each target to reduce the CT-to-body divergence.

Figure 3:
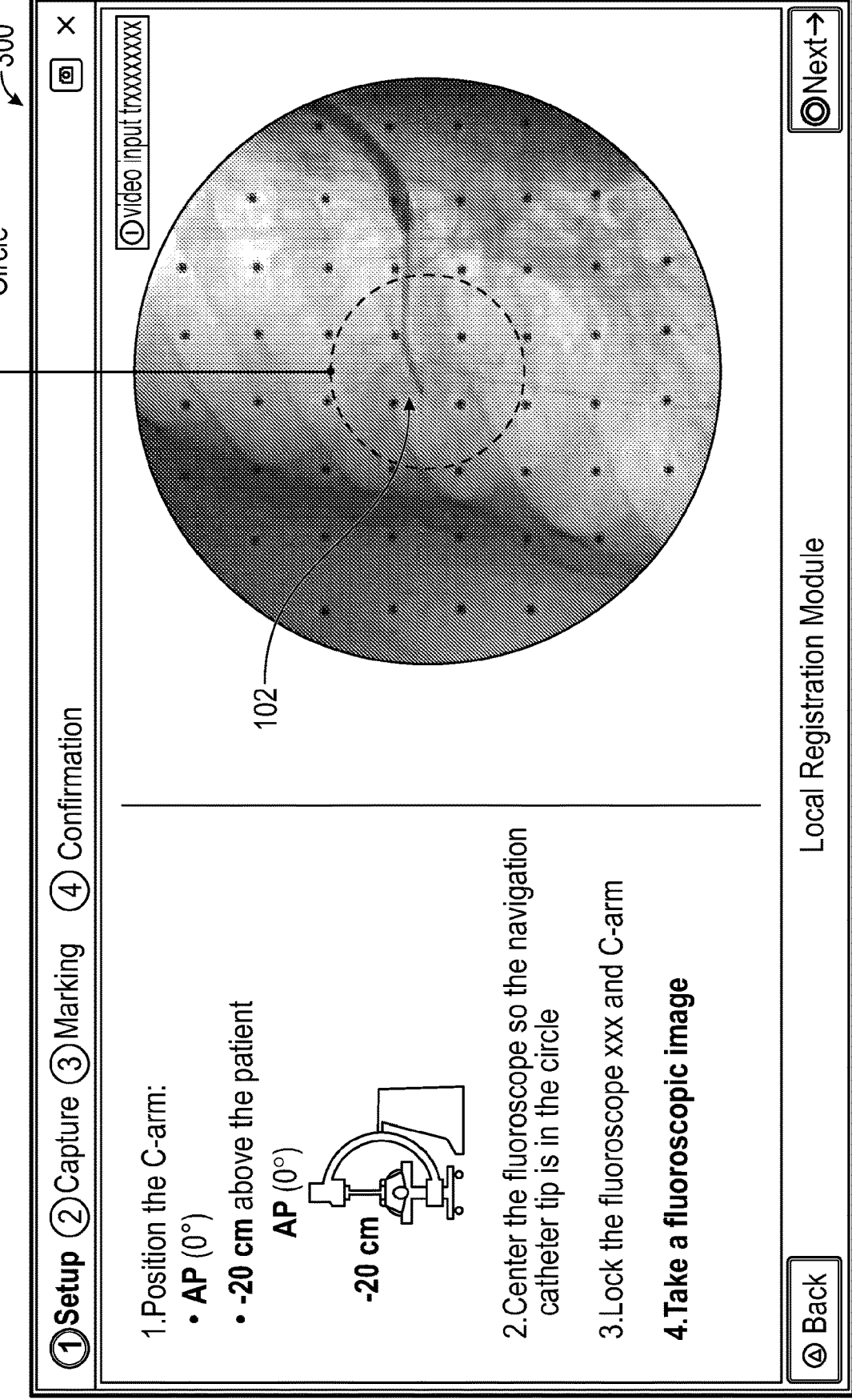
FIG. 3 is a user interface of a navigation program in accordance with aspects of the disclosure.
Figure 4:
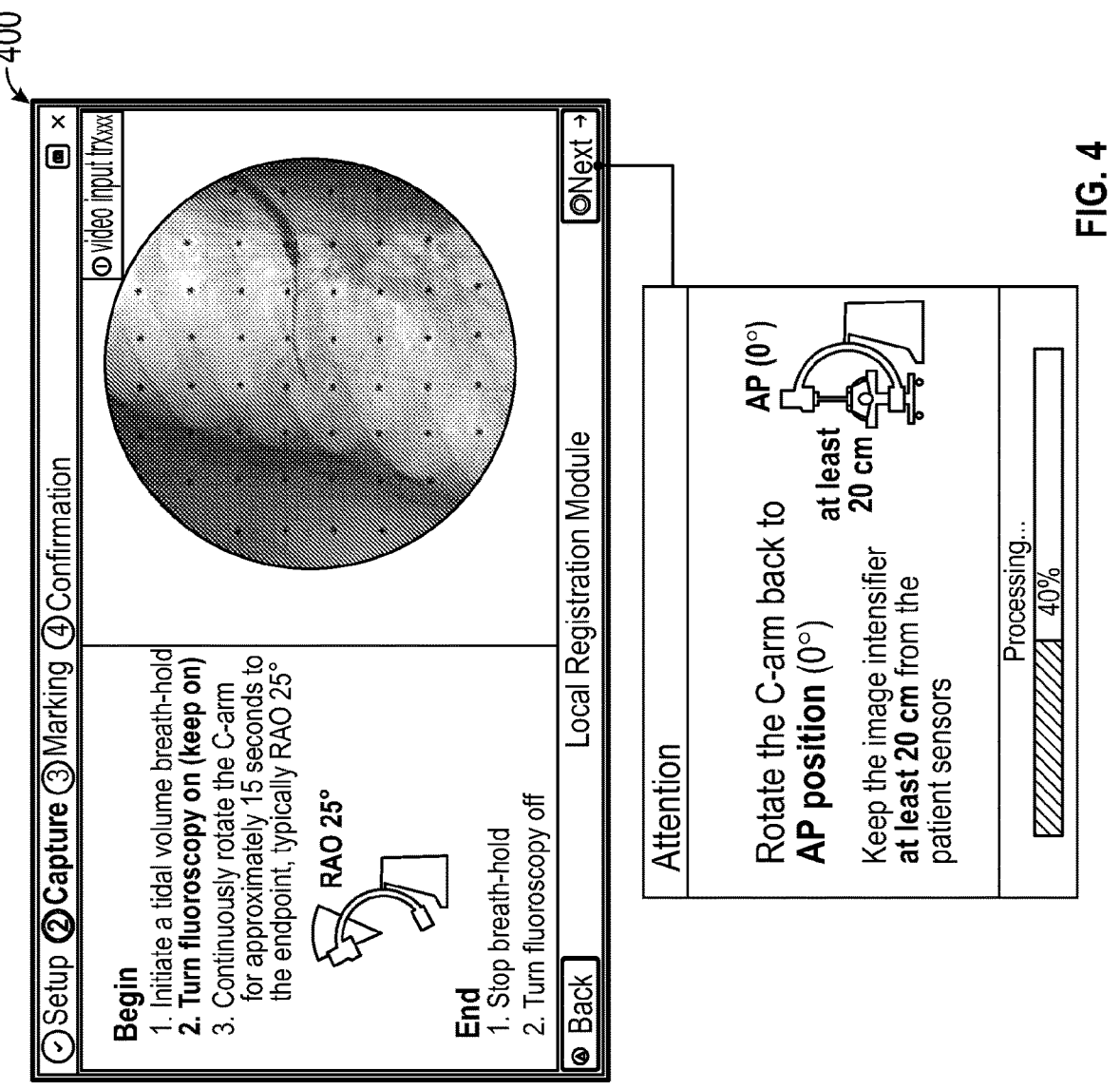
FIG. 4 is a user interface of a navigation program in accordance with aspects of the disclosure.
Figure 5:
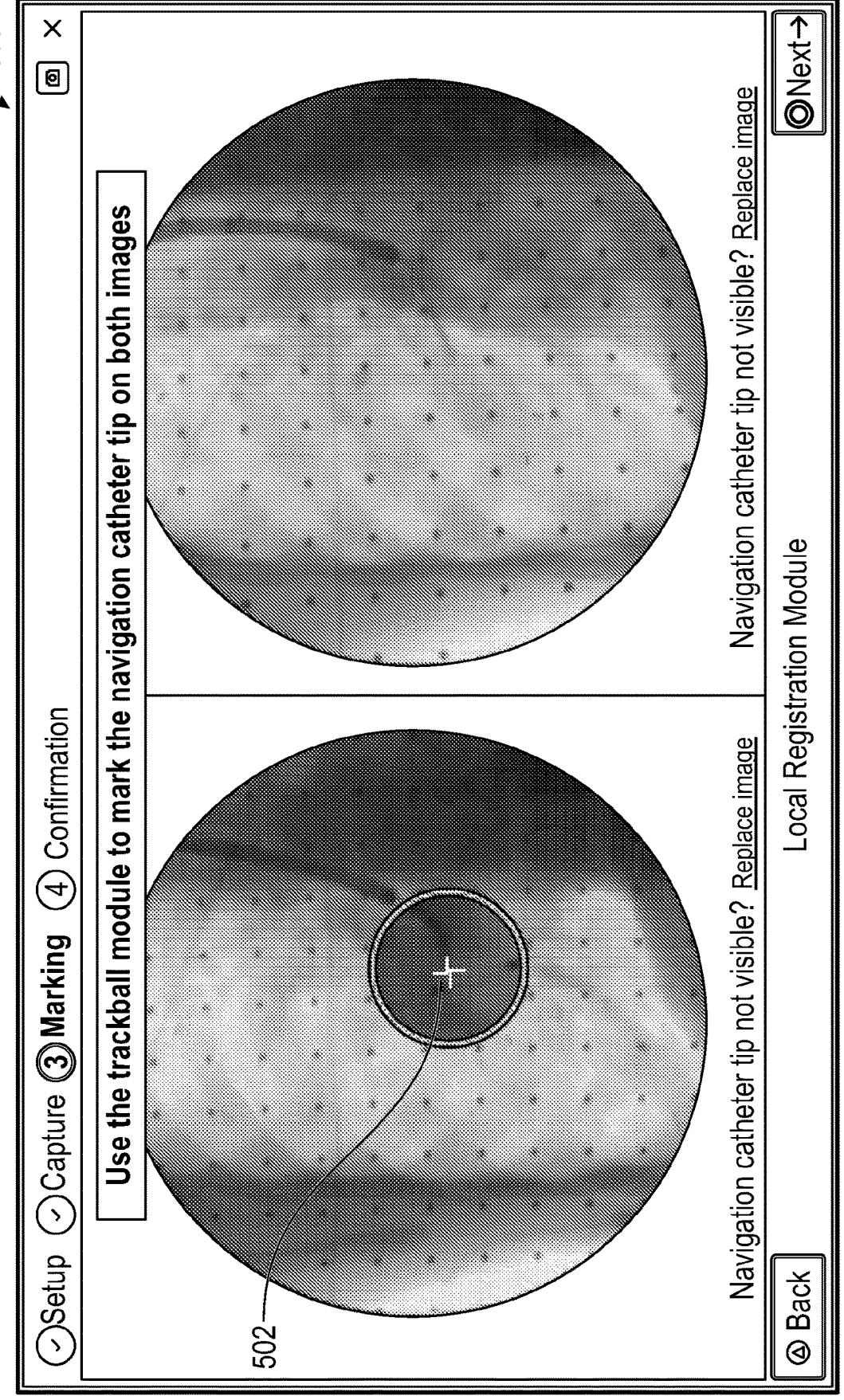
FIG. 5 is a user interface of a navigation program in accordance with aspects of the disclosure.

One aspect of the disclosure is the presentation of a breath hold reminder. As depicted in FIG. 2 a "Breath Hold Initiated? Confirm" button 204 needs to be selected by the clinician before any intraprocedural imaging can be commenced. Once selected, a tracker described in greater detail below is initiated to track the movement of the sensor 104 or 126 within the patient during the imaging. Once the tracker is initiated, a 2D fluoroscopic image of the catheter 102 is acquired for the marking of the area of the catheter 102 as shown in FIG. 3, for example, by arranging a circle such that the end of the catheter 102 is proximate the center of the circle. Next, as depicted in FIG. 4, a sequence of fluoroscopic images captured via fluoroscopic imaging device 124 for example from about 25 degrees on one side of the AP position to about 25 degrees on the other side of the AP position. A fluoroscopic 3D reconstruction may be then generated by the computing device 122. The generation of the fluoroscopic 3D reconstruction is based on the sequence of fluoroscopic images and the projections of structure of markers incorporated with transmitter mat 120 on the sequence of images. Following generation of the fluoroscopic 3D reconstruction, two fluoroscopic images are displayed in the GUI on computing device 122, as shown in FIG. 5. As depicted the GUI 500 in FIG. 5, the end of the catheter 102 needs to be marked using a marker 502 in each of these images. The two images are taken from different portions of the fluoroscopic 3D reconstruction. The fluoroscopic images of the 3D reconstruction may be presented on the user interface in a scrollable format where the user is able to scroll through the slices in series if desired.

Figure 6:
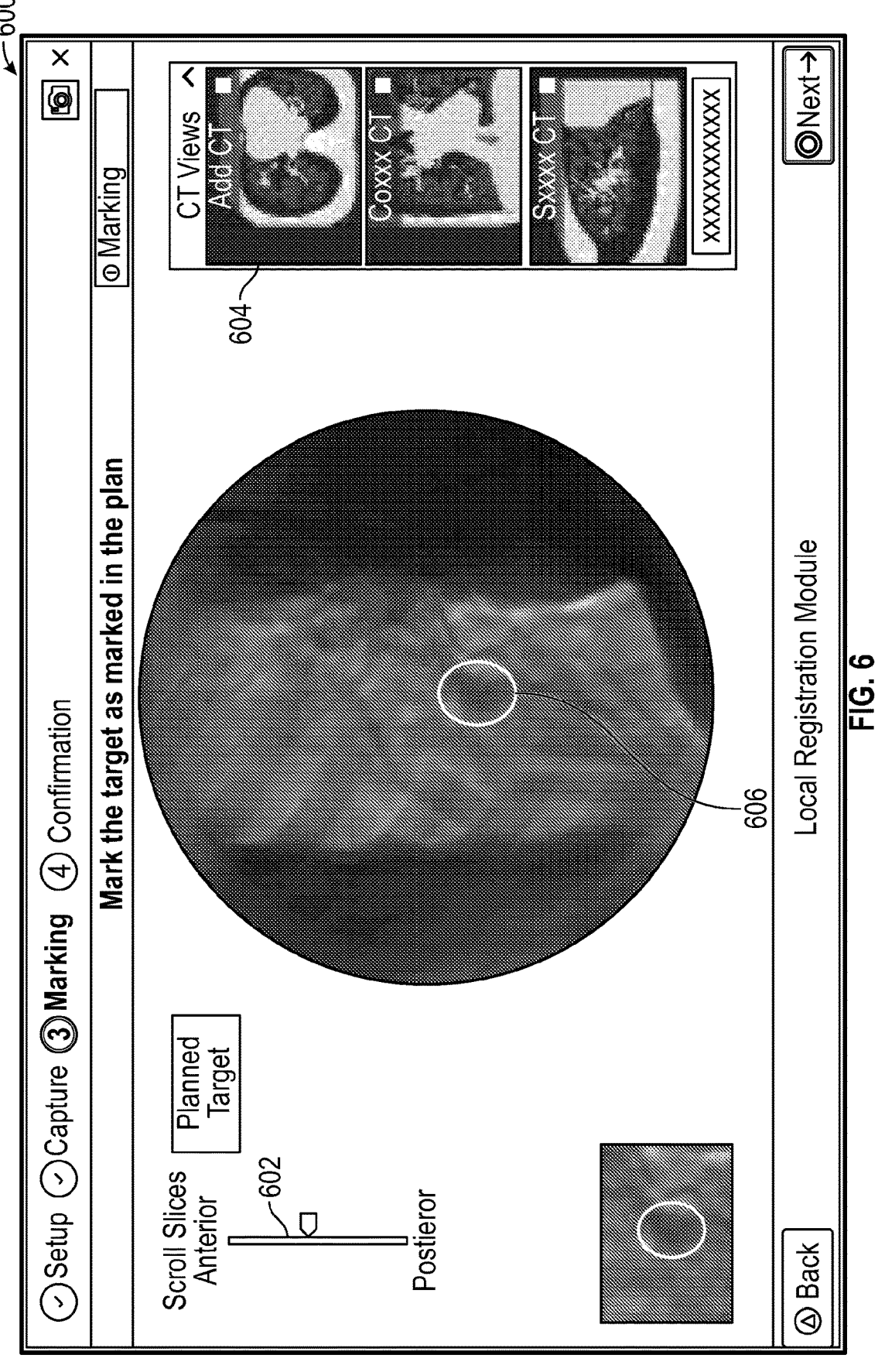
FIG. 6 is a user interface of a navigation program in accordance with aspects of the disclosure.

Next as depicted in FIG. 6, the clinician is directed to identify and mark the target in the fluoroscopic 3D reconstruction in GUI 600. A scroll bar 602 allows the clinician to scroll through the fluoroscopic 3D reconstruction until the target is identified. CT views 604 may also be displayed to assist in identifying the position of the target. Once identified, a marker 606 is placed on the target.

Figure 7:
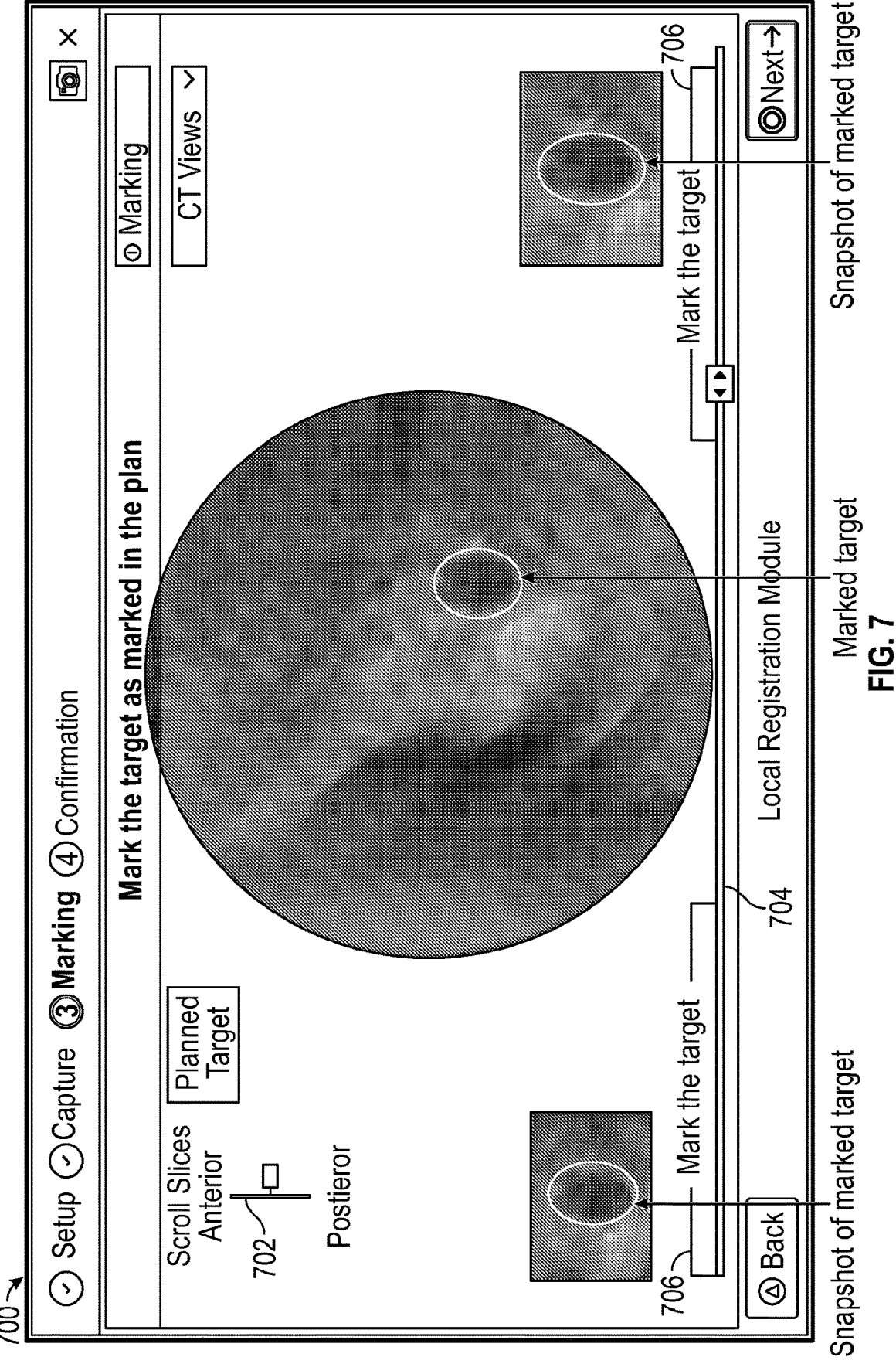
FIG. 7 is a user interface of a navigation program in accordance with aspects of the disclosure.
Figure 8:
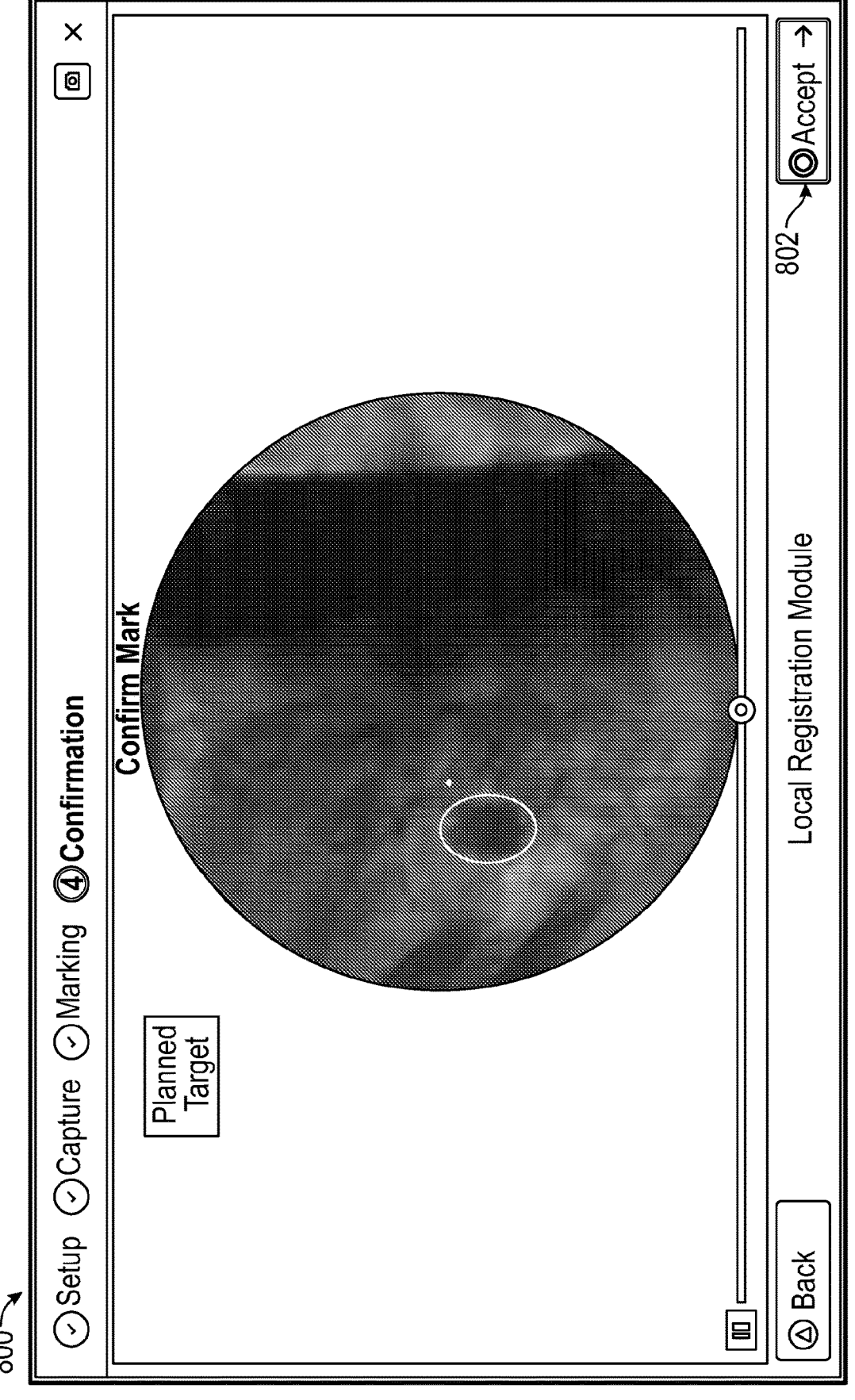
FIG. 8 is a user interface of a navigation program in accordance with aspects of the disclosure.

Following the marking of the target in GUI 600, the clinician will be asked to mark the target in two different perspectives in GUI 700 of FIG. 7. Again, a scroll bar 702 allows for changes of the depth of the fluoroscopic image being displayed so the target can be found in the fluoroscopic 3D reconstruction. A second scrollbar 704 allows for translation or rotation though the fluoroscopic 3D reconstruction to reach the two perspectives in which the target is to be marked. The portion of the fluoroscopic 3D reconstruction in which the target is to be marked is identified by zone markers 706. Once the target is marked in each perspective, a thumbnail image of that perspective with the target marked is displayed proximate the zone markers 706. Once complete, the clinician is presented with a GUI 800 in FIG. 8 where the entire fluoroscopic 3D reconstruction may be viewed to ensure that the target or lesion remains within the marker 802 through the fluoroscopic 3D reconstruction.

Figure 9:
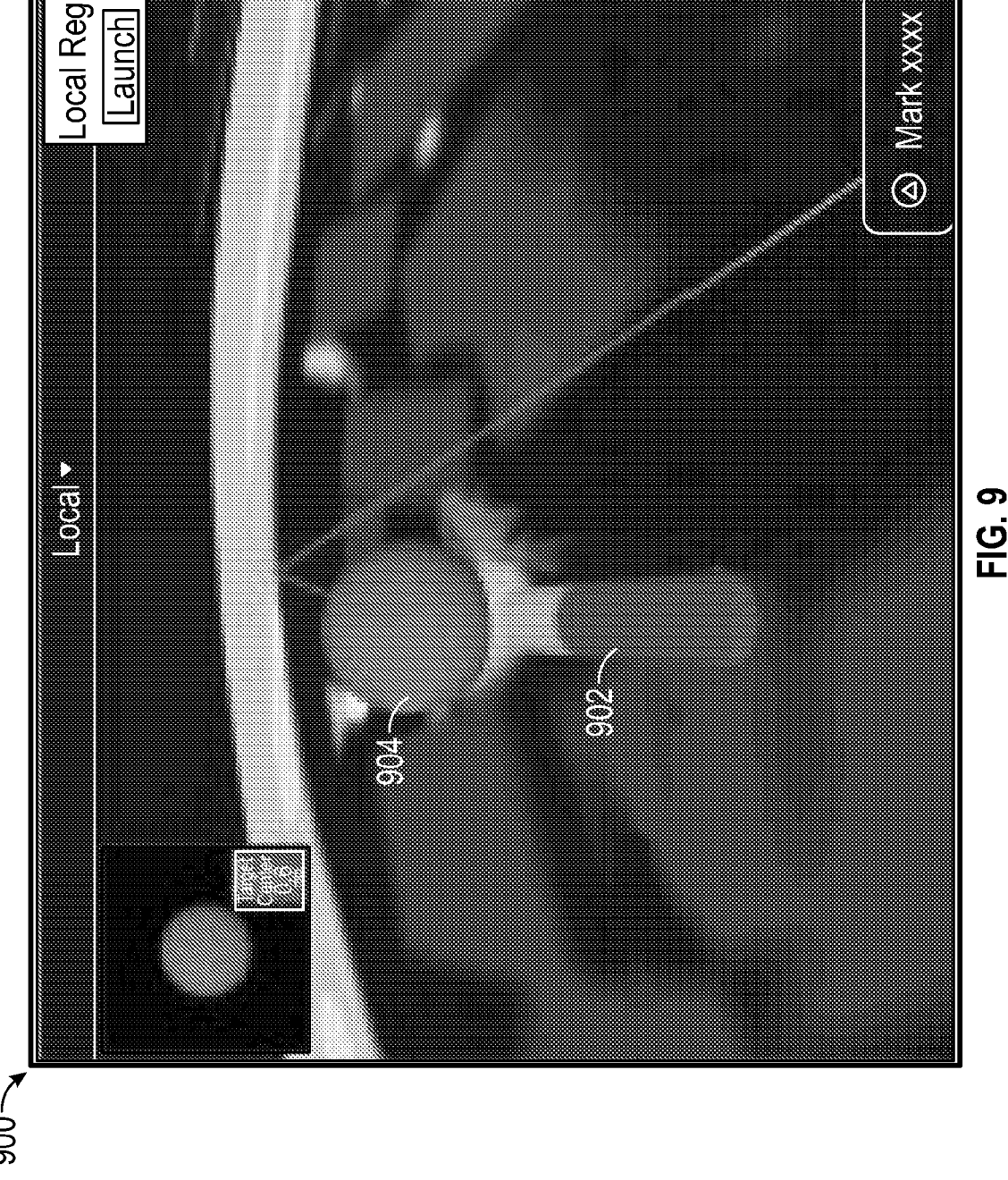
FIG. 9 is a user interface of a navigation program in accordance with aspects of the disclosure.

After confirming that there are marks on the target throughout the fluoroscopic 3D reconstruction, the clinician may select the "Accept" button 802, at which point the local registration process ends and the relative position of the catheter 102 in the 3D model and the pathway plan is updated to display the actual current relative position of the end of the catheter 102 and the target. By the local registration process the offset between the location of the target and the tip of the catheter 102 is determined as they are observed in the fluoroscopic 3D reconstruction. The offset is utilized, via computing device 122, to correct any errors in the original registration process and minimize any CT-to-body divergence. As a result, the location and/or orientation of the navigation catheter on the GUI with respect to the target is updated. This update is seamless to the clinician, and a GUI 900 is presented in computer device 122 as depicted in FIG. 9 with the updated relative positions of the location of the catheter 102 represented by a virtual catheter 902 and the target 904. At this point the clinician has a high degree of confidence that the catheter 102 is at the location relative to the target as displayed in the GUI 900.

By the process described above the relative positions of the catheter 102 and the target are marked in the 3D fluoroscopic reconstruction and the offset determined. In addition, the position of the catheter 102 is always being sensed either in the EM field to provide EM coordinates of its position, or in robotic coordinates if a robot is employed. As a result of the combination of the offset with the detection of position of the catheter 102, EM field coordinates or robotic coordinates of the target can be defined.

Figure 10A:
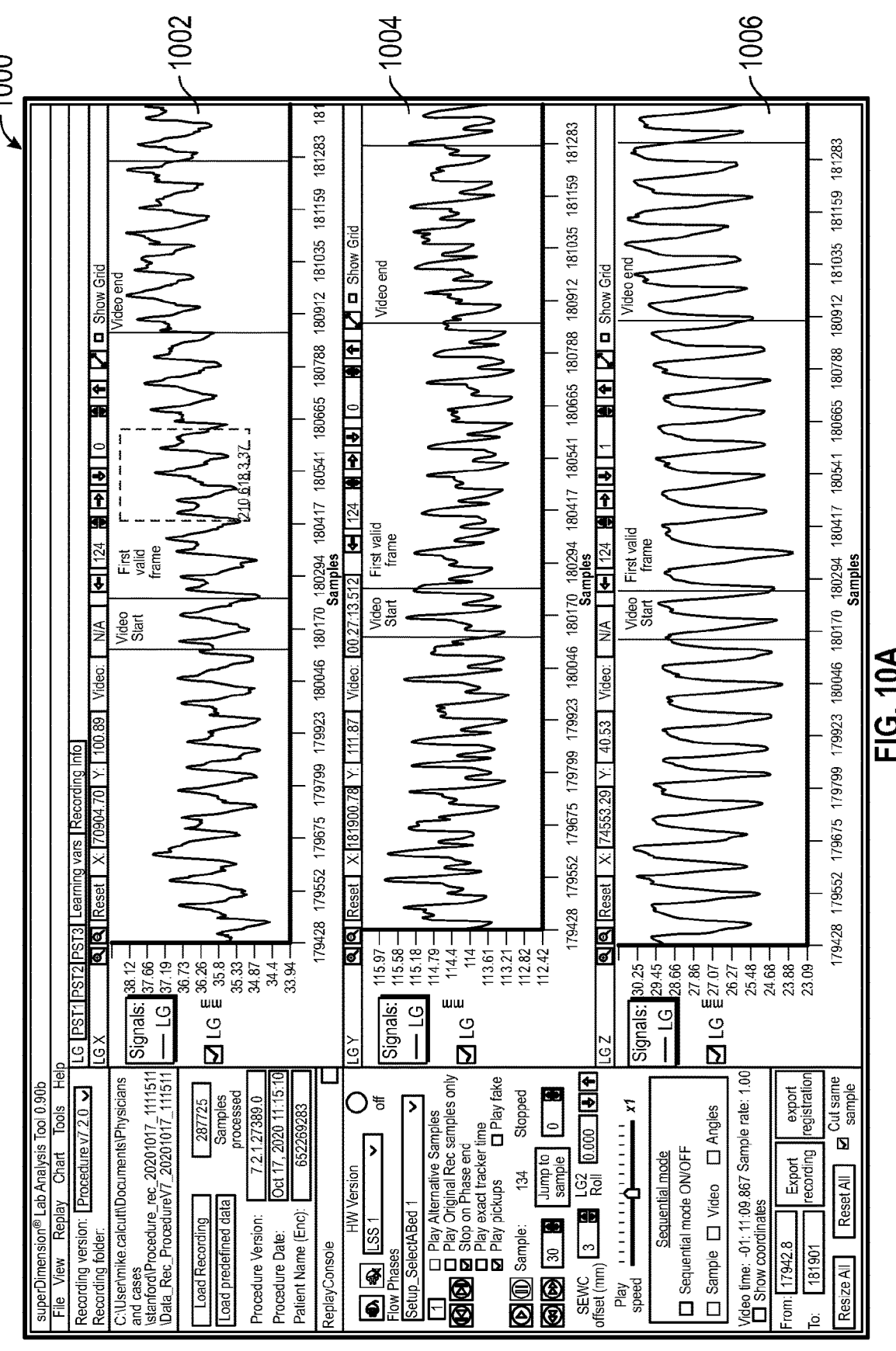
FIG. 10A is a user interface depicting three graphs of movement of a sensor in the X, Y, and Z directions in accordance with the disclosure.

However, as noted above, the relative position of the catheter 102 and target as shown in FIG. 9 is typically determined while the patient is at a breath hold condition to minimize the movement of the catheter 102 in the fluoroscopic imaging. During breath hold, the sensor 104 or 126 in the catheter 102 or LG still moves to some extent. As an initial matter, when breath hold is initiated, the pressure of the air within the lungs stabilizes and causes the lungs to change shape depending on the relative pressure of the areas of the lungs at the time the breath hold is undertaken until the lungs reach a plateau. FIG. 10A depicts a UI 1000 showing the movement of a sensor 104 or 126 near the distal end of the catheter 102 during normal tidal volume breathing. The UI 1000 includes graphs 1002, 1004, 1006 for the movement of the sensor 104, 126 in each of the X, Y, and Z directions. As can be seen in the graph, the movement senor 104 or 126 is relatively constant in each of the X, Y, and Z directions with the majority of movement being caused by respiration that is controlled by a ventilator. A secondary portion of the movement is caused by the patient's heartbeat. In FIG. 10A the movement in the X direction (i.e., movement from the left side to the right side of the body as the patient is resting supine on the transmitter mat 120) is depicted by graph 1002. The movement in the Y-direction (i.e., movement posterior to anterior with increasing values being movement anterior) is depicted in the graph 1004. Finally, the movement in the Z-direction (i.e., movement the head to feet direction with increasing values indicating movement towards the head) is depicted in graph 1006. Though generally described with respect to the sensors 104, 126 a similar determination utilizing the reference sensors 118 placed on the exterior of a patient's chest and within the EM field generated by the transmitter mat 120.

Figure 10B:
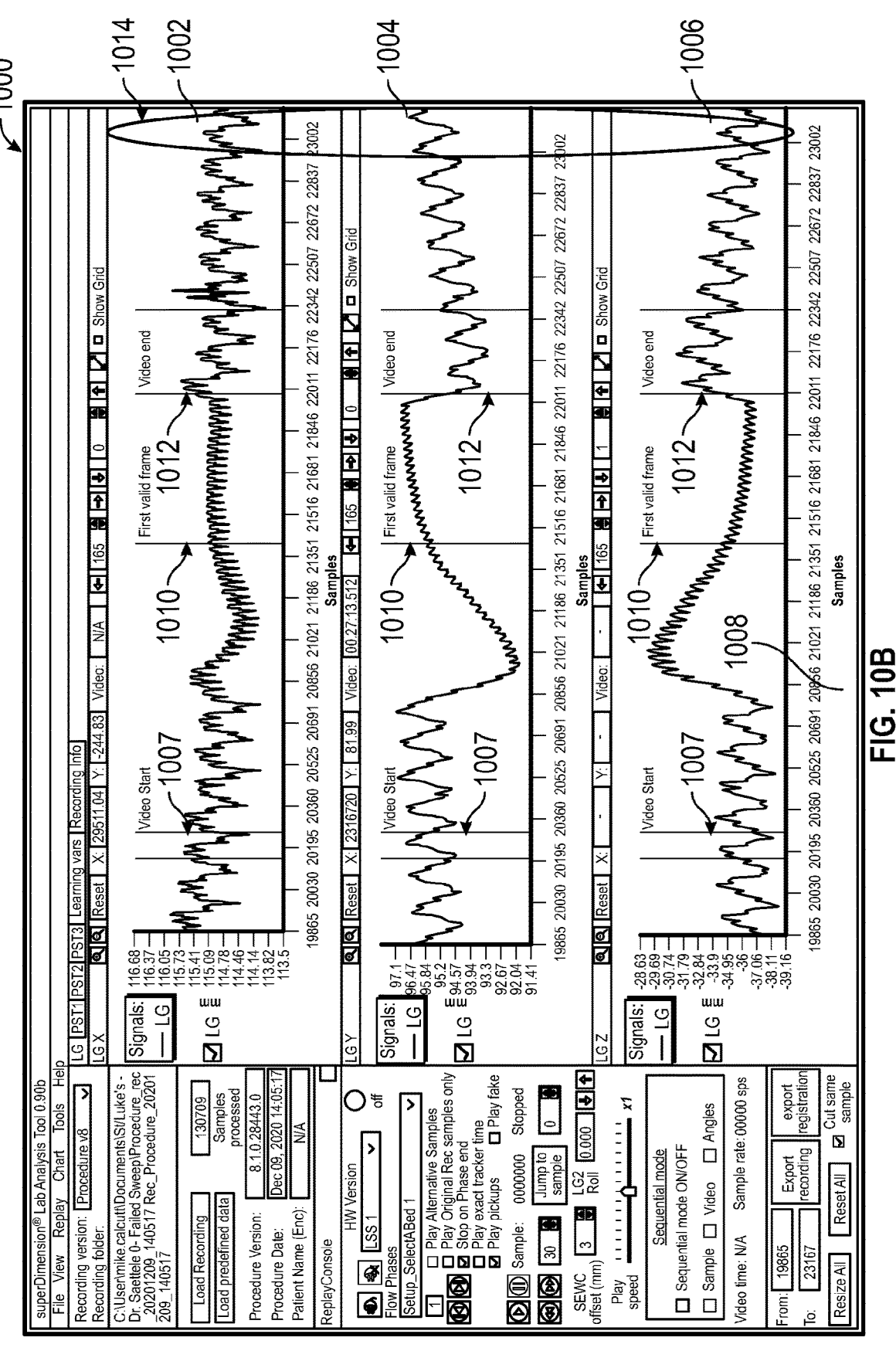
FIG. 10B is a user interface depicting three graphs of movement of a sensor in the X, Y, and Z directions during a breath hold in accordance with the disclosure.

FIG. 10B is substantially similar to FIG. 10A, except that at a point 1008, in each of the graphs 1002-1006, the breath hold is initiated. As this breath hold is initiated the position of sensor 104, 126 within the patient moves as the air pressure within the lungs stabilizes. As can be seen there is little movement in the X-direction, but an initial movement of 1-3 mm in both the Y and Z directions. This movement takes a few seconds to reach a plateau 1010 at which the movement in any one direction is less than about 0.5 mm and is substantially the result of the heartbeat of the patient. Note the continued cyclic motion of the sensor 104, 126 despite breath hold and the reaching of the plateau.

In accordance with one aspect of the disclosure, once a plateau is achieved as depicted at point 1010 in each graph 1002-1006, the GUI 400 could display a "Breath hold plateau achieved." This notification may be associated with allowing the clinician to begin rotation of the C-arm of the imaging device 124. However, generally imaging is initiated before the breath hold is initiated at point 1007 and the achieving of a plateau at point 1010. The breath hold plateau achieved determination provides a time in the video of the imaging at which the data acquired can reasonably be used for volumetric 3D reconstruction and provide usable data for local registration.

Figure 10C:
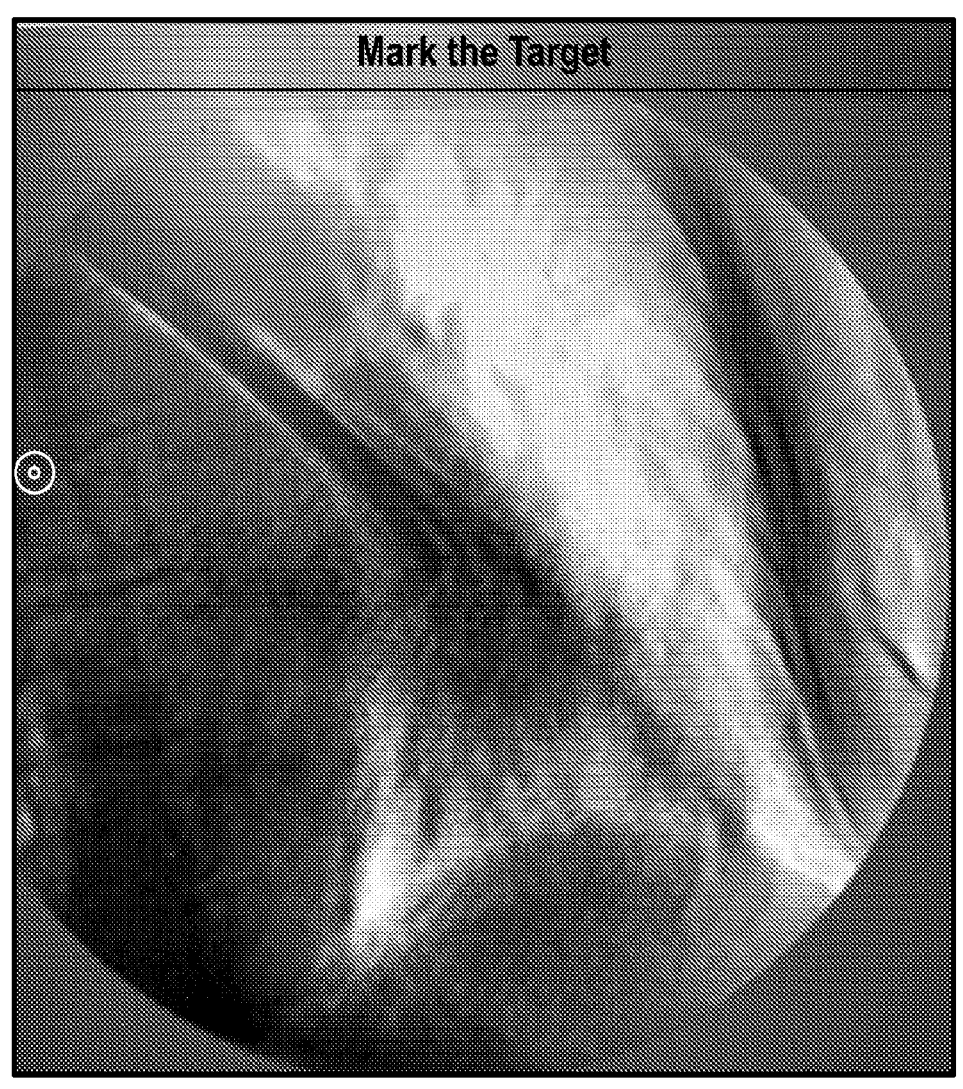
FIG. 10C is an image captured by a fluoroscopic imaging device where no breath hold was initiated.

Alternatively, where the imaging device 124 is separate from rest of the navigation system, no such interlock may be possible to prevent the imaging during tidal volume breathing. Should imaging occur without a breath hold, while the patient is still in tidal volume breathing, as depicted in FIG. 10A the images for analysis in GUI 500 or GUI 600 would be like those depicted in FIG. 10C, which are obviously too blurry to allow for determination of the location of the catheter 102 or target within the images.

However, the clinician may not actually know that no breath hold has been undertaken prior to initiation of the imaging. By monitoring the position of the sensor 104, 126 the application may determine that there was no change in the position or the movement of the sensor 104, 126 at any time prior to clicking on the "Next" button 402 on GUI 400. If no change is detected in the position or movement of the sensor 104, 126 the application may present an alert on the GUI 500 that no breath hold was initiated, and thus no images are displayed in the GUI 500. Still further, the failure to undertake a breath hold may remain unknown to the clinician through the procedure, images may be displayed in GUI 500 and 600 for marking as outlined above, but the existence of a breath hold or the sufficiency of the breath hold, is only analyzed after the procedure to determine whether there is a likelihood of the biopsy or therapy device having been accurately placed or to make determinations of why a biopsy or therapy device failed to be properly placed to reach the target.

As noted above, performing imaging during a breath hold with as little movement as possible will provide the cleanest images with which to undertake the review described with respect to FIGS. 2-9 and while confirmation of the undertaking of a breath hold during that process is one aspect of the disclosure, it is not the only aspect of the breath hold analysis. Another aspect of the disclosure is determination of the timing following a return to normal tidal volume breathing when the sensor 104, 126 (and therewith the patient's lungs) have returned to their pre-breath hold position and inflation states. Still a further aspect of the disclosure is directed to determining the magnitude of the movement of the sensor 104, 126 in each of the X-Y-Z directions while undertaking a breath hold. Similarly, another aspect of the disclosure is directed to determining that the volume of the lungs upon returning to normal tidal volume breathing has changed from the pre-breath hold volume to a post breath hold volume.

For example, in one aspect of the disclosure, as can be seen with respect to FIG. 10B, normal tidal volume breathing is re-initiated at point 1012 however, the position of the sensor 104, 126 does not immediately return to its pre-breath hold position within the patient (and in actuality within the EM field) for some time. As can be seen following point 1012 while movement caused by breathing is seen in the graphs 1002-1006, the average detected position of the sensor 104, 126 generally drifts back to the pre-breath hold position and achieves this position some time interval after the return of tidal volume breathing.

In a perfect patient scenario, the after breath hold movement of the sensor 104, 126 would mirror the pre-breath hold movement of the sensor, and return the sensor 104, 126 to the same location it was in prior to the breath hold such. However, perfect return is not necessarily required for the methods described here. At point 1014 a return to substantially the same position, within a range of acceptability (margin), is observed. In one aspect of the disclosure an indicator can be provided on FIG. 9 stating "Returned to Normal Breathing" and displayed. This can indicate to the clinician that they can have confidence that there has not been any significant change in the location of the physiology of the patient because of the breath hold and local registration process. In addition, this can indicate to the clinician that they can have confidence that further actions, e.g., biopsy or therapy can be achieved using the determined relative positions of the local registration process. In part this is due to the proximity of the target 202 to the sensor 104, 126. In one aspect of the disclosure, the movement of the sensor 104, 126 and the movement of the target during the breath hold procedure is assumed to be substantially the same. Thus, the relative location and orientation of the sensor 104, 126 (i.e., the end of the catheter 102) to the target as calculated during the breath hold is assumed to be approximately the same after the breath hold as long as the position of the sensor 104,126 returns to the pre-breath hold position, within some margin of error.

Figure 11:
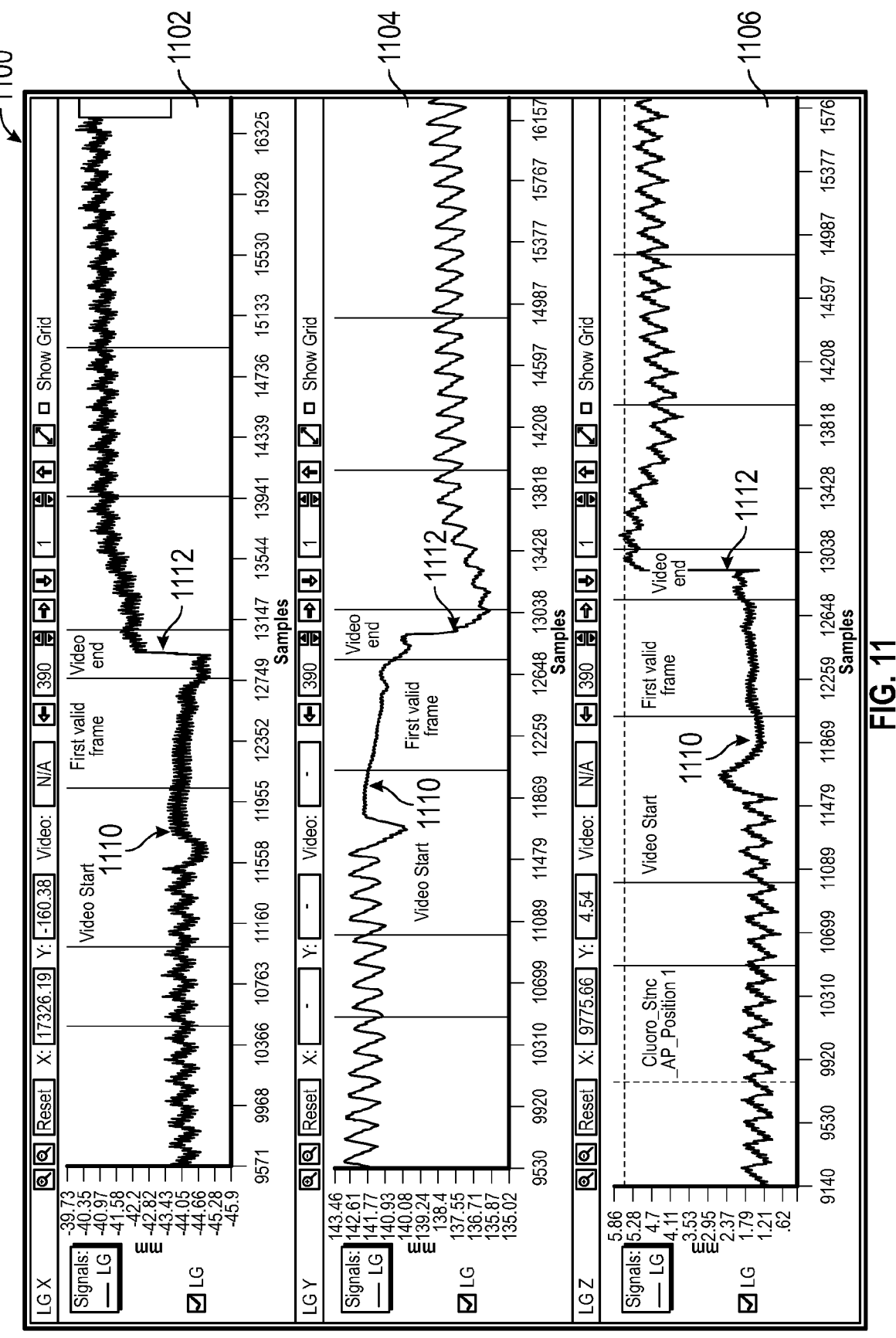
FIG. 11 is a disclosure is a user interface depicting three graphs of movement of a sensor in the X, Y, and Z directions where the sensor did not return to a pre-breath hold position after release in accordance with the disclosure.

The assumptions described above, however, are only valid if following the breath hold the lung and substantially returns to the same volume as it had prior to the breath hold. FIG. 11 depicts the graphs of the position of a sensor 104, 126 in X, Y, Z dimensions similar to FIG. 10B. However, as can be seen following initiation of the breath hold at point 1108 the location of the sensor 104, 126 in each of the graphs 1102, 1104, 1106 is at one position. Following plateau at 1110 and subsequent release of the breath hold at point 1112, the sensor 104, 126 does not return to the same location as prior to the breath hold in any of the X, Y, or Z directions. Instead, as can be seen following breath hold point 1112, the sensed location of the sensor 104, 126 has moved approximately has moved approximately 3 mm in the X direction, approximately 7 mm in the Y direction and approximately 3.5 mm in the Z direction as depicted in the new tidal volume breathing portion 1116 of the UI 1100. As can be seen this position is quite different than the location sensed prior to the breath hold and indicates that the lung volume has changed dramatically from the lung volume prior to the breath hold. As a result, the clinician cannot have any confidence that the relative position of the catheter 102 and target 202 as calculated during the local registration is accurate.

In one aspect of the disclosure, the UI 1100 or GUI 900 may present an error notification or messaging to the clinician that the breath hold procedure resulted in some change in lung volume and needs to be redone, or that the anesthesiologist needs to adjust the lung volume settings of the ventilation apparatus to return the lung volume to the pre-breath hold positions to the extent possible. In the event the anesthesiologist is able to return the patient to normal tidal volume breathing with the sensor at approximately the pre-breath hold position, the biopsy or therapy can continue as normal. An indicator of a return to the pre-breath hold position may then be displayed on GUI 900 and the procedure (e.g., biopsy or therapy) may be continued. If a return is not possible, the local registration process of FIGS. 2-9 may need to be performed again. An indicator may be presented on the GUI 900 to alert the clinician of the need to re-perform the local registration process.

Figure 12:
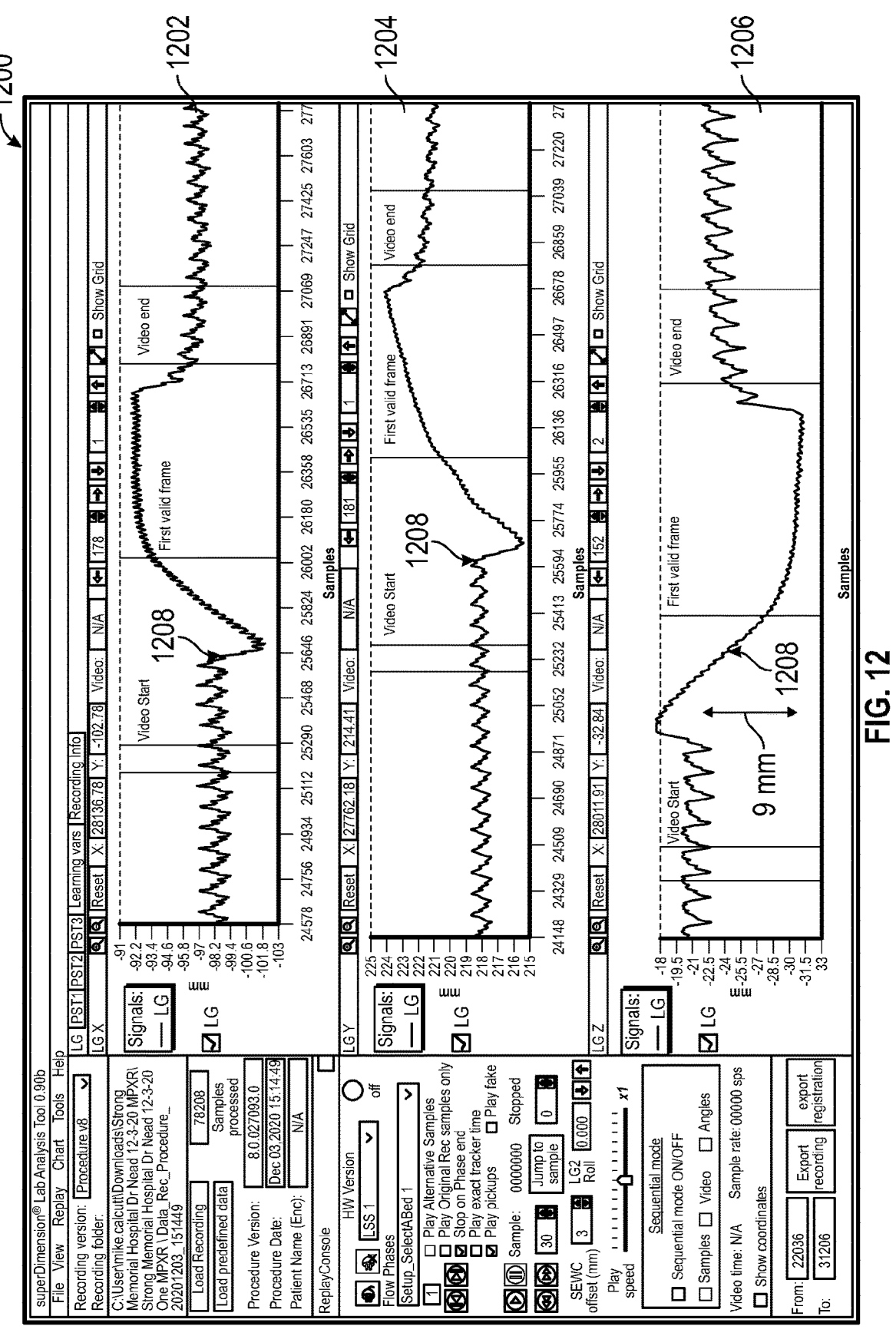
FIG. 12 is a user interface depicting three graphs of movement of a sensor in the X, Y, and Z directions during a breath hold, where breath hold resulted in a large change in position of the sensor in accordance with the disclosure.

However, lack of return to substantially the pre-breath hold position is not the only factor to consider with respect to the breath hold. Other factors include the magnitude of the movement of the sensor 104, 126 from the pre-breath hold tidal volume position to the breath hold plateau 1010 position. For example, in FIG. 12, the UI 1200 depicts graphs 1202-1206 showing the movement of the sensor 104, 126 as a result of a breath hold initiated at point 1208. As is clear, particularly with respect to the graph 1206, the sensor 104, 126 moves approximately 9 mm. Such a move may indicate a significant change in the volume of the lungs due to the breath hold. This large change in volume of the lungs reduces the confidence that the sensor 104, 126 and the target are actually moving substantially together and remain in a substantially constant relative position and orientation. Accordingly, when such a change in position of the sensor 104, 126 is detected, an alert may be presented on GUI 400 or GUI 500 indicating that the breath hold resulted in too great a change in location of the sensor 104, 126 to achieve useful local registration.

A method of utilizing the breath hold information as described above with respect to FIGS. 10A-12 is described with reference to FIG. 13. The method 1300 starts during with navigation of a catheter 102 to a position proximate the target 202 and that proximity is displayed on GUI 200 as depicted in FIG. 2 at step 1302. In accordance with one embodiment following display of the proximity of the of the catheter 102 and the target 202, imaging is initiated at step 1304. This initiation of imaging before a breath hold can be seen in, for example, the UI 1000 where imaging is commenced during normal tidal volume breathing (e.g., at point 1001). Following, initiating of imaging, a breath hold can be initiated at step 1306, this corresponds to point 1008 in FIG. 10A. At step 1308 the position and movement of the sensor 104, 126 is monitored and at step 1310 a determination is made whether a plateau point 1010 in FIG. 10A, has been reached. If the plateau has not been reached then the monitoring continues, but if it has been reached an indication of reaching the plateau may be displayed on for example GUI 400 at step 1312. If imaging has not already been initialized at step 1304, imaging may be initialized now at step 1314. At step 1316, a determination can be made as to the extent of the movement of the sensor caused by the breath hold at step 1306 to reach the plateau at step 1310. Those of skill in the art will recognize that steps 1314 and 1316 may be switched in order. If the determination at step 1316 is that the movement exceeds a threshold, a threshold that will lead to inaccuracy in further procedures if the relative positions of the catheter 102 and the target in the 3D volumetric reconstruction of the images are employed for the local registration, the imaging is stopped at step 1318. The breath hold is stopped as well at step 1320. Note step 1320 may occur before step 1318 without departing from the scope of the disclosure. The patient is then allowed to return to normal tidal volume breathing at step 1322 and the method returns to step 1304 to try and achieve an acceptable breath hold again.

If, however, the determination at step 1316 is that the movement of the sensor 104, 126 is within the threshold for movement the method moves to step 1324 where imaging is ceased. This cessation follows sufficient rotation of the C-arm of the imaging device 124 to capture images sufficient to generate a 3D volumetric reconstruction, as described above. Following cessation of the imaging at step 1324 the breath hold can be ended at step 1326. The order of steps 1324 and 1326 may be reversed without departing from the scope of the disclosure. After the breath hold is released at step 1324, the position of the sensor is monitored at step 1328. At step 1330 a determination is made whether the sensor 104, 126 has returned to a pre-breath hold position, within a range of tolerance. If the sensor 104, 126 has not yet returned to the pre-breath hold position a location error message may be displayed on the GUI 400 or 500 before allowing the local registration process to progress. If at any point it is determined that the sensor 104, 126 has returned to the pre-breath hold position, within some tolerance, the method progresses to step 1324, where an indication of a successful return to the pre-breath hold position is displayed on the GUI 400 or 500. The method then allows the local registration to be finalized (e.g., the steps described in connection with FIGS. 5-9) at step 1326. Following finalization of the local registration, the GUI 900 is displayed with the virtual catheter 902 depicted relative to the target 904 based on the local registration and the method ends at step 1328. Alternatively, if after some time the position of the sensor 104, 126 cannot be returned to the pre-breath hold position the local registration process can be restarted at step 1330 and the method returns to step 1304.

Figure 13:
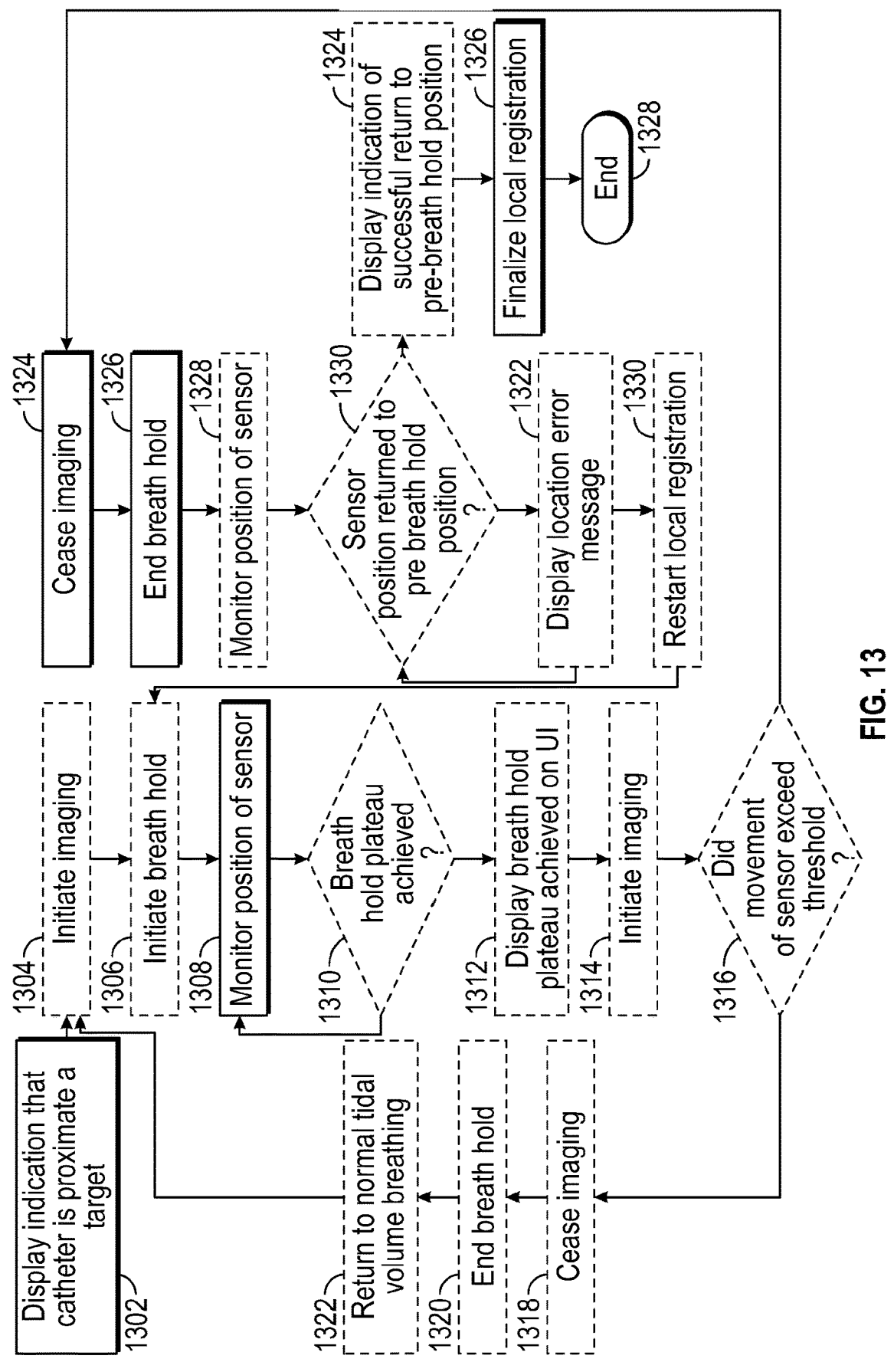
FIG. 13 is a flow chart for analysis of the sufficiency of a breath hold in accordance with the disclosure.

It should be noted that any steps described herein which are shown in FIG. 13 in dashed boxes are optional steps that may or may not be included in a method in accordance with the disclosure. Further, though the UIs 1000-1200 are depicted as three separate graphs such presentation may me confusing or provide too much information to the clinician who is engaged in an already complex procedure. Accordingly, the UIs may not be presented to the clinician in this form but may be presented as a single composite graph formed of for example graphs 1002, 1004, 1006. Such composite graph allows for quick determination of the concepts of achieving the breath hold plateau 1010, and the return to the pre-breath hold position of the sensor 104, 126 following release of the breath hold. Still further, though described herein with respect to volumetric 3D reconstruction of fluoroscopic images, the disclosure is not so limited. The imaging device 124 may be for example a cone-beam computed tomography (CBCT) imaging device or another imaging device capable of interprocedurally imaging the patient. The CBCT imaging device allows for a determination of the relative position of the catheter 102 and the target to perform the determination of their relative positions and to update the displayed position of the catheter relative to the target in 3D models derived from pre-procedural CT images. Another aspect of the disclosure is that though described above in connection with electromagnetic (EM) sensors in the catheter 102, the sensor 104, 126 is not so limited. The sensor 104, 126 may alternatively be shape sensor such as fiber-Bragg grating, an ultrasonic sensor, an accelerometer, an inertial measurement unit, or others without departing from the scope of the disclosure.

Figure 14:
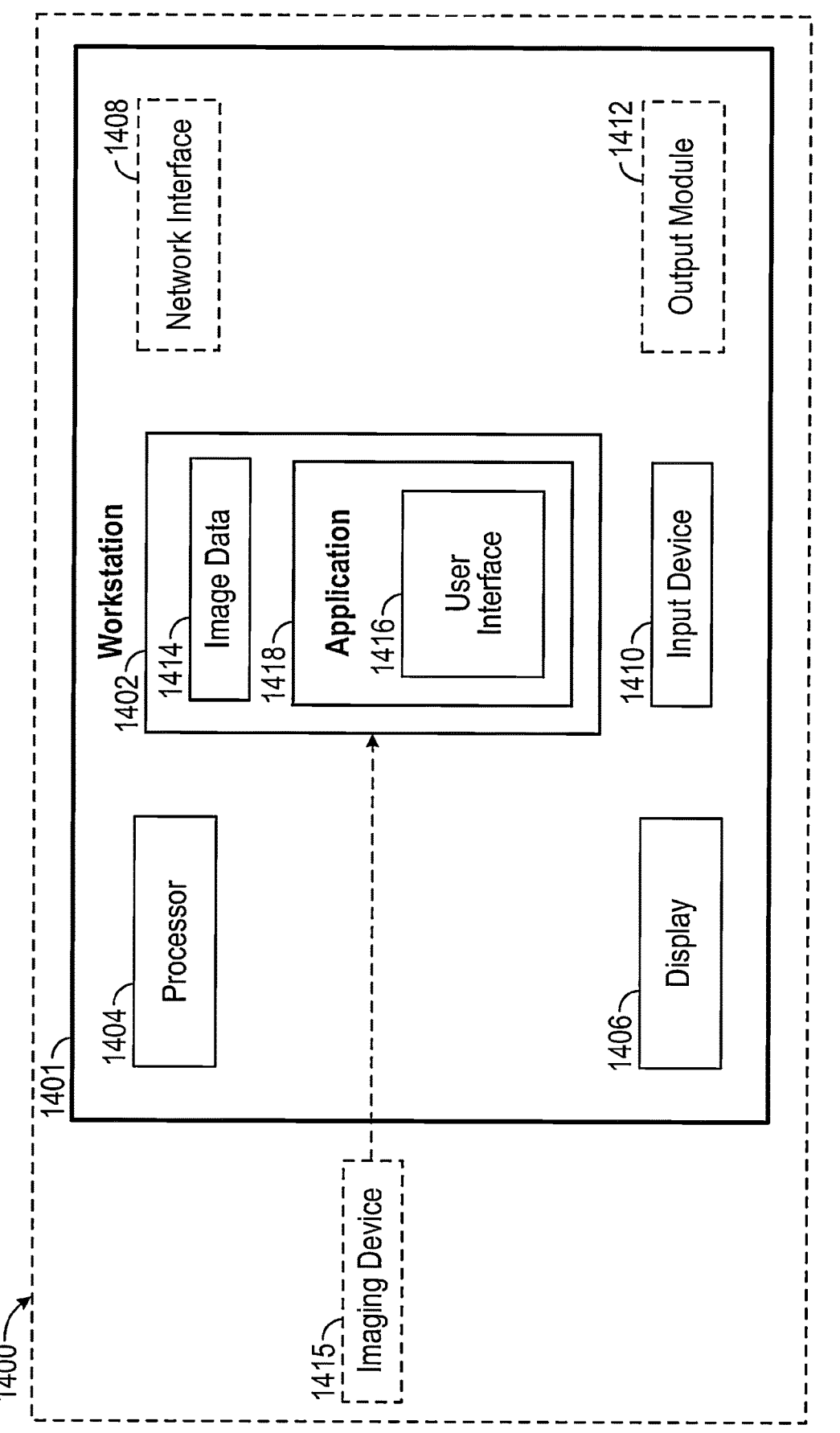
FIG. 14 is a schematic view of a computing device in accordance with aspects of the disclosure.

Reference is now made to FIG. 14, which is a schematic diagram of a system 1400 configured for use with the methods of the disclosure including the method of FIG. 13. System 1400 may include a workstation 1401, and optionally a fluoroscopic imaging device or fluoroscope 1415. In some embodiments, workstation 1401 may be coupled with fluoroscope 1415, directly or indirectly, e.g., by wireless communication. Workstation 1401 may include a memory 1402, a processor 1404, a display 1406 and an input device 1410. Processor or hardware processor 1404 may include one or more hardware processors. Workstation 1401 may optionally include an output module 1412 and a network interface 1408. Memory 1402 may store an application 1418 and image data 1414. Application 1418 may include instructions executable by processor 1404 for executing the methods of the disclosure including the method of FIG. 13.

Application 1418 may further include a user interface 1416. Image data 1414 may include the CT scans, the generated fluoroscopic 3D reconstructions of the target area and/or any other fluoroscopic image data and/or the generated one or more slices of the 3D reconstruction. Processor 1404 may be coupled with memory 1402, display 1406, input device 1410, output module 1412, network interface 1408 and fluoroscope 1415. Workstation 1401 may be a stationary computing device, such as a personal computer, or a portable computing device such as a tablet computer. Workstation 1401 may embed a plurality of computer devices.

Memory 1402 may include any non-transitory computer-readable storage media for storing data and/or software including instructions that are executable by processor 1404 and which control the operation of workstation 1401 and, in some embodiments, may also control the operation of fluoroscope 1415. Fluoroscope 1415 may be used to capture a sequence of fluoroscopic images based on which the fluoroscopic 3D reconstruction is generated and to capture a live 2D fluoroscopic view according to this disclosure. In an embodiment, memory 1402 may include one or more storage devices such as solid-state storage devices, e.g., flash memory chips. Alternatively, or in addition to the one or more solid-state storage devices, memory 1402 may include one or more mass storage devices connected to the processor 1404 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 1404. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 1401.

Application 1418 may, when executed by processor 1404, cause display 1406 to present user interface 1416. User interface 1416 may be configured to present to the user a single screen including a three-dimensional (3D) view of a 3D model of a target from the perspective of a tip of a medical device, a live two-dimensional (2D) fluoroscopic view showing the medical device, and a target mark, which corresponds to the 3D model of the target, overlaid on the live 2D fluoroscopic view, as shown, for example, in FIG. 2. User interface 1416 may be further configured to display the target mark in different colors depending on whether the medical device tip is aligned with the target in three dimensions.

Network interface 1408 may be configured to connect to a network such as a local area network (LAN) consisting of a wired network and/or a wireless network, a wide area network (WAN), a wireless mobile network, a Bluetooth network, and/or the Internet. Network interface 1408 may be used to connect between workstation 1401 and fluoroscope 1415. Network interface 1408 may be also used to receive image data 1414. Input device 1410 may be any device by which a user may interact with workstation 1401, such as, for example, a mouse, keyboard, foot pedal, touch screen, and/or voice interface. Output module 1412 may include any connectivity port or bus, such as, for example, parallel ports, serial ports, universal serial busses (USB), or any other similar connectivity port known to those skilled in the art. From the foregoing and with reference to the various figures, those skilled in the art will appreciate that certain modifications can be made to the disclosure without departing from the scope of the disclosure.

While detailed embodiments are disclosed herein, the disclosed embodiments are merely examples of the disclosure, which may be embodied in various forms and aspects. For example, embodiments of an electromagnetic navigation system, which incorporates the target overlay systems and methods, are disclosed herein; however, the target overlay systems and methods may be applied to other navigation or tracking systems or methods known to those skilled in the art. Therefore, specific structural and functional details disclosed herein are not to be interpreted as limiting, but merely as a basis for the claims and as a representative basis for teaching one skilled in the art to variously employ the disclosure in virtually any appropriately detailed structure.

We claim:

1. A system comprising:
a catheter having a distal portion including a sensor; and
a computing device including a processor and a computer readable recording medium storing instructions that when executed by the processor cause the computing device configured to:
receive signals from the sensor to determine a position of the distal portion of the catheter;
receive live fluoroscopic video images of the catheter proximate a target;
monitor a position of the sensor to determine whether a breath-hold plateau has been achieved;
determine whether movement of the sensor has exceeded a threshold to achieve the breath-hold plateau;
cease live fluoroscopic video image video acquisition; and
monitor the position of the sensor, to determine whether the sensor position has returned to a pre-breath-hold position, wherein upon determination that the sensor has returned to the pre-breath-hold position:
determine a relative position of the catheter and the target at multiple instances in the fluoroscopic video;
calculate a position of the target in a coordinate system of the sensor; and
update a displayed position of the distal portion of the catheter with respect to the target in a three-dimensional (3D) model.

2. The system of claim 1, wherein the 3D model is derived from a pre-procedure computed tomography (CT) image data.

3. The system of claim 1, wherein the sensor is an electromagnetic sensor.

4. The system of claim 1, wherein the position of the target is calculated based on a calculated offset and the determined position of the catheter.

5. The system of claim 1, wherein reception of a first of the live fluoroscopic video images is configured to occur before a breath hold is begun.

6. A method of improving a quality of images for local registration, comprising:
initializing imaging of a catheter and a target;
monitoring a position of a sensor on the catheter to determine whether a breath-hold plateau has been achieved;
determining whether movement of the sensor has exceeded a threshold to achieve the breath-hold plateau;
ceasing imaging; and
monitoring the position of the sensor, to determine whether the sensor has returned to a pre-breath hold position, wherein upon determination that the sensor has returned to the pre-breath-hold position;
determining a relative position of the sensor and a target at multiple instances in images;
calculating a position of the target in a coordinate system of the sensor; and
updating a displayed position of a distal end of the catheter with respect to the target in a three-dimensional (3D) model.

7. The method of claim 6, further comprising initiating a breath hold of a patient after the initializing of the imaging.

8. The method of claim 6, further comprising ceasing breath hold prior to determining whether the sensor has returned to the pre-breath-hold position.

9. The method of claim 6, wherein if the movement of the sensor to reach the breath hold plateau exceeds the threshold the method further comprises:
ending a breath hold;
returning to tidal volume breathing; and
reinitializing imaging.

10. The method of claim 6, wherein if the position of the sensor does not return to the pre-breath-hold position local registration is restarted.

11. The method of claim 6, further comprising:
determining a position of the target in the images; and
calculating an offset between the distal end of the catheter and the target.

12. The method of claim 11, wherein the 3D model is derived from a pre-procedure computed tomography (CT) image data.

13. A method of navigating a catheter to a desired location within a luminal network comprising:
receiving a computed tomography (CT) image data set;
identifying one or more targets in the CT image data set;
generating a three-dimensional (3D) model of the luminal network and pathway to the one or more targets;
registering the 3D model and the pathway to the luminal network;
updating a position of the catheter in the 3D model as the catheter is advanced along the pathway;
performing a local registration to determine a relative position of the catheter and one of the one or more targets;
acquiring a fluoroscopic image of the luminal network;
monitoring a position of a sensor associated with the catheter to determine whether a breath hold plateau has been achieved;
determining whether movement of the sensor has exceeded a threshold to achieve the breath hold plateau;
ceasing fluoroscopic image acquisition; and
monitoring the position of the sensor, to determine whether the sensor has returned to a pre-breath hold position, wherein upon determination that the sensor has returned to the pre-breath hold position:

determining a position of the one of the one or more targets and the catheter in the fluoroscopic image;

detecting the position of the sensor on a distal portion of the catheter;

calculating a position of the one of the one or more targets in a coordinate system of the sensor; and updating a displayed position of the distal portion of the catheter with respect to the one of the one or more targets in the 3D model.

14. The method of claim 13, wherein the sensor is an electromagnetic sensor.

15. The method of claim 13, wherein the sensor is a fiber-Bragg grating shape sensor.

16. The method of claim 13, wherein the position of the one or more targets is calculated based on a calculated offset between the determined position of the catheter in the fluoroscopic image and the detected position of the sensor.

17. The method of claim 13, further comprising initiating a breath hold of a patient after acquisition of the fluoroscopic image.

18. The method of claim 13, further comprising ending a breath hold prior to determining whether the sensor has returned to the pre-breath hold position.

19. The method of claim 13, wherein if movement of the sensor to reach the breath hold plateau exceeds the threshold the method further comprises:

ending a breath hold;

returning to tidal volume breathing; and reinitializing imaging.

20. The method of claim 13, wherein if the position of the sensor does not return to the pre-breath hold position the local registration is restarted.

* * * * *